United States Patent
Wang et al.

(10) Patent No.: US 11,267,887 B2
(45) Date of Patent: *Mar. 8, 2022

(54) ANTI-CTLA-4 ANTIBODIES

(71) Applicant: Agency For Science, Technology and Research, Connexis (SG)

(72) Inventors: Cheng-I Wang, Singapore (SG); Eve Ngoh, Singapore (SG); Siok Ping Yeo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 503 days.

This patent is subject to a terminal disclaimer.

(21) Appl. No.: 16/099,652

(22) PCT Filed: Apr. 13, 2017

(86) PCT No.: PCT/EP2017/058956
§ 371 (c)(1),
(2) Date: Nov. 7, 2018

(87) PCT Pub. No.: WO2017/194265
PCT Pub. Date: Nov. 16, 2017

(65) Prior Publication Data
US 2019/0153097 A1 May 23, 2019

(30) Foreign Application Priority Data
May 10, 2016 (SG) .............. 10201603721T

(51) Int. Cl.
| | |
|---|---|
| *A61K 39/395* | (2006.01) |
| *A61K 39/00* | (2006.01) |
| *C07K 16/42* | (2006.01) |
| *C07K 16/46* | (2006.01) |
| *C07K 16/28* | (2006.01) |
| *A61K 9/00* | (2006.01) |
| *A61P 31/00* | (2006.01) |
| *A61P 35/00* | (2006.01) |
| *A61K 35/17* | (2015.01) |
| *C12N 5/0783* | (2010.01) |
| *C12N 15/85* | (2006.01) |
| *G01N 33/574* | (2006.01) |

(52) U.S. Cl.
CPC ........ *C07K 16/2818* (2013.01); *A61K 9/0019* (2013.01); *A61K 35/17* (2013.01); *A61P 31/00* (2018.01); *A61P 35/00* (2018.01); *C12N 5/0638* (2013.01); *C12N 15/85* (2013.01); *A61K 2039/505* (2013.01); *C07K 2317/33* (2013.01); *C07K 2317/56* (2013.01); *C07K 2317/565* (2013.01); *C07K 2317/76* (2013.01); *C07K 2317/92* (2013.01); *C07K 2319/00* (2013.01); *G01N 33/574* (2013.01)

(58) Field of Classification Search
None
See application file for complete search history.

(56) References Cited

U.S. PATENT DOCUMENTS 9,758,583 B2 * 9/2017 Wang .............. A61P 35/00

FOREIGN PATENT DOCUMENTS

WO  WO 01/14424 A2  3/2001

OTHER PUBLICATIONS

Jacobs T, Graefe SE, Niknafs S, Gaworski I, Fleischer B. Murine malaria is exacerbated by CTLA-4 blockade. J Immunol. 2002;169:2323-9. (Year: 2002).*
Lepenies B, Gaworski I, Tartz S, Langhorne J, Fleischer B, Jacobs T. CTLA-4 blockade differentially influences the outcome of non-lethal and lethal Plasmodium yoelii infections. Microbes Infect. 2007;9:687-94. (Year: 2007).*
Cecchinato V, Tryniszewska E, Ma ZM, et al. Immune activation driven by CTLA-4 blockade augments viral replication at mucosal sites in simian immunodeficiency virus infection. J Immunol. 2008;180:5439-47. (Year: 2008).*
Raue' and Slifka. Pivotal Advance: CTLA-4 T cells exhibit normal antiviral functions during acute viral infection. J. Leukoc. Biol. 81:1165-1175; 2007 (Year: 2007).*
Grosso, et al., "CTLA-4 blockade in tumor models: an overview of preclinical and translational research". Cancer Immunity (Jan. 22, 2013) vol. 13, p. 5.
Hanson, et al., "Preclinical in vitro characterization of anti-CTLA4 therapeutic antibody CP-675,206". Proc. Amer Assoc Cancer Res (2004) 64:877.
Hoogenboom, "Selecting and screening recombinant antibody libraries". Nature Biotechnology 23, 1105-1116 (2005).
International Search Report, PCT/EP2017/0589956 dated Jun. 27, 2017, 11 pages.
R and D Systems, Human CTLA-4 antibody "Description Species Reactivity Human", Dec. 31, 2012, retrieved from the internet URL:https://resources.mdsystems.com/pdfs/datasheets/mab325.pdf [retrieved on Jun. 15, 2017].
Sansom, "CD28, CTLA-4 and their ligands: who does what and to whom?" Immunology 2000, 101: 169-177.
Wolchok, et al., "Development of ipilimumab: a novel immunotherapeutic approach for the treatment of advanced melanoma", Ann NY Acad Sci., pp. 1-13.
International Preliminary Report on Patentability for Application No. PCT/EP2017/058956, dated Sep. 19, 2018.
Wolchok et al., The mechanism of anti-CTLA-4 activity and the negative regulation of T-cell activation. Oncologist. 2008;13 Suppl 4:2-9. doi: 10.1634/theoncologist.13-S4-2.

(Continued)

*Primary Examiner* — Maher M Haddad
(74) *Attorney, Agent, or Firm* — Wolf, Greenfield & Sacks, P.C.

(57) ABSTRACT

Anti-CTLA-4 antibodies are disclosed. Also disclosed are compositions comprising such antibodies, and uses and methods using the same.

14 Claims, 16 Drawing Sheets

Specification includes a Sequence Listing.

(56) References Cited

OTHER PUBLICATIONS

Ye et al., T-cell exhaustion in chronic hepatitis B infection: current knowledge and clinical significance. Cell Death Dis. Mar. 19, 2015;6(3):e1694. doi: 10.1038/cddis.2015.42.

* cited by examiner

2C8 clone

DIQLTQSPSSVSASVGDRVTITC<u>RATQGISSWLA</u>WYQQKPGKAPKLLIY<u>AASSLQS</u>
GVPSRFSGSGSGTEFTLTISSLQPEDFATYYC<u>QQANTLPLFT</u>FGPGTKVDIK (SEQ ID NO: 1)

LC-CDR1:   RATQGISSWLA   (SEQ ID NO:5)
    LC-CDR2:   AASSLQS   (SEQ ID NO:6)
    LC-CDR3:   QQANTLPLFT   (SEQ ID NO:7)

2C8_gl clone

DIQMTQSPSSVSASVGDRVTITC<u>RATQGISSWLA</u>WYQQKPGKAPKLLIY<u>AASSLQS</u>
GVPSRFSGSGSGTDFTLTISSLQPEDFATYYC<u>QQANTLPLFT</u>FGPGTKVDIK (SEQ ID NO: 2)

LC-CDR1:   RATQGISSWLA   (SEQ ID NO:5)
    LC-CDR2:   AASSLQS   (SEQ ID NO:6)
    LC-CDR3:   QQANTLPLFT   (SEQ ID NO:7)

Figure 1

2C8 clone

QVQLQQSGPGLVKPSQTLSLTCAISGDTVSSNTAAWNWIRQSPSRGLEWLGRTYY
RSKWYSDYGLSVKSRMTINADTSKNQVSLHLNSVTPEDTAVYYCAREGSGGTLIY
WGQGTLVTVSS (SEQ ID NO: 3)

HC-CDR1:    SNTAAWN    (SEQ ID NO:8)
    HC-CDR2:    RTYYRSKWYSDYGLSVKS    (SEQ ID NO:9)
    HC-CDR3:    EGSGGTLIY    (SEQ ID NO:10)

2C8_gl clone

QVQLQQSGPGLVKPSQTLSLTCAISGDSVSSNTAAWNWIRQSPSRGLEWLGRTYY
RSKWYSDYGLSVKSRITINPDTSKNQFSLQLNSVTPEDTAVYYCAREGSGGTLIYW
GQGTLVTVSS (SEQ ID NO: 4)

HC-CDR1:    SNTAAWN    (SEQ ID NO:8)
    HC-CDR2:    RTYYRSKWYSDYGLSVKS    (SEQ ID NO:9)
    HC-CDR3:    EGSGGTLIY    (SEQ ID NO:10)

Figure 2

Light chain variable domains

2C8 clone

>2C8_aa_L
DIQLTQSPSSVSASVGDRVTITCRATQGISSWLAWYQQKPGKAPKLLIYAASSLQS
GVPSRFSGSGSGTEFTLTISSLQPEDFATYYCQQANTLPLFTFGPGTKVDIK [SEQ
ID NO:1]

>2C8_ntd_L
GACATCCAGTTGACCCAGTCTCCATCTTCTGTGTCTGCATCTGTGGGAGACAGA
GTCACCATCACTTGTCGGGCGACTCAGGGTATAAGCAGCTGGTTAGCCTGGTA
TCAGCAGAAACCAGGGAAAGCCCCTAAGCTCCTGATCTATGCTGCATCCAGTTT
GCAAAGTGGGGTCCCATCCAGGTTCAGCGGCAGTGGCTCTGGGACAGAGTTC
ACTCTCACTATCAGCAGCCTGCAGCCTGAAGATTTTGCAACTTACTATTGTCAAC
AGGCTAATACTCTCCCCTTATTCACTTTCGGCCCTGGGACCAAAGTGGATATCA
AA [SEQ ID NO:11]

2C8_gl clone

>2C8_gl_aa_L
DIQMTQSPSSVSASVGDRVTITCRATQGISSWLAWYQQKPGKAPKLLIYAASSLQS
GVPSRFSGSGSGTDFTLTISSLQPEDFATYYCQQANTLPLFTFGPGTKVDIK [SEQ
ID NO:2]

>2C8_gl_ntd_L
GACATCCAGATGACCCAGTCTCCATCTTCTGTGTCTGCATCTGTGGGAGACAGA
GTCACCATCACTTGTCGGGCGACTCAGGGTATAAGCAGCTGGTTAGCCTGGTA
TCAGCAGAAACCAGGGAAAGCCCCTAAGCTCCTGATCTATGCTGCATCCAGTTT
GCAAAGTGGGGTCCCATCCAGGTTCAGCGGCAGTGGCTCTGGGACAGATTTCA
CTCTCACTATCAGCAGCCTGCAGCCTGAAGATTTTGCAACTTACTATTGTCAACA
GGCTAATACTCTCCCCTTATTCACTTTCGGCCCTGGGACCAAAGTGGATATCAA
A [SEQ ID NO:12]

Figure 3

Heavy chain variable domains

2C8 clone

>2C8_aa_H
QVQLQQSGPGLVKPSQTLSLTCAISGDTVSSNTAAWNWIRQSPSRGLEWLGRTYY
RSKWYSDYGLSVKSRMTINADTSKNQVSLHLNSVTPEDTAVYYCAREGSGGTLIY
WGQGTLVTVSS [SEQ ID NO:3]

>2C8_ntd_H
CAGGTACAGCTGCAGCAGTCAGGTCCAGGACTGGTGAAGCCCTCGCAGACCC
TCTCACTCACCTGCGCCATCTCCGGGGACACTGTCTCTAGCAACACTGCTGCTT
GGAATTGGATCAGGCAGTCCCCCTCGAGAGGCCTTGAGTGGCTGGGAAGGAC
ATACTACAGGTCCAAGTGGTATAGTGACTATGGACTATCTGTGAAAAGTCGGAT
GACCATCAATGCAGACACATCCAAGAACCAGGTCTCCCTACACCTGAACTCTGT
AACTCCCGAAGACACGGCTGTATATTACTGTGCAAGAGAGGGCAGTGGCGGAA
CTTTGATCTACTGGGGCCAGGGAACCCTGGTCACCGTCTCAAGC [SEQ ID
NO:13]

2C8_gl clone

>2C8_gl_aa_H
QVQLQQSGPGLVKPSQTLSLTCAISGDSVSSNTAAWNWIRQSPSRGLEWLGRTYY
RSKWYSDYGLSVKSRITINPDTSKNQFSLQLNSVTPEDTAVYYCAREGSGGTLIYW
GQGTLVTVSS [SEQ ID NO:4]

>2C8_gl_ntd_H
CAGGTACAGCTGCAGCAGTCAGGTCCAGGACTGGTGAAGCCCTCGCAGACCC
TCTCACTCACCTGCGCCATCTCCGGGGACAGTGTCTCTAGCAACACTGCTGCTT
GGAATTGGATCAGGCAGTCCCCCTCGAGAGGCCTTGAGTGGCTGGGAAGGAC
ATACTACAGGTCCAAGTGGTATAGTGACTATGGACTATCTGTGAAAAGTCGGAta
ACCATCAATCCAGACACATCCAAGAACCAGTTCTCCCTACAGCTGAACTCTGTA
ACTCCCGAAGACACGGCTGTATATTACTGTGCAAGAGAGGGCAGTGGCGGAAC
TTTGATCTACTGGGGCCAGGGAACCCTGGTCACCGTCTCAAGC [SEQ ID NO:14]

Figure 3 (cont.)

ANTI-CTLA-4 ANTIBODIES

CROSS-REFERENCE TO RELATED APPLICATIONS

This application claims priority to and is a 35 U.S.C. § 371 national phase application of PCT/EP2017/058956 (WO2017/194265), filed on Apr. 13, 2017 entitled "Anti-CTLA-4 Antibodies", which application claims priority to and the benefit of Singapore Patent Application No. 10201603721T, filed May 10, 2016 the disclosures of which are incorporated herein by reference in their entirety.

SEQUENCE STATEMENT

Incorporated by reference herein in its entirety is the Sequence Listing entitled "Sequence_listing" created May 10, 2016, size of 9 kilobytes.

FIELD OF THE INVENTION

The present invention relates to antibodies that bind to cytotoxic T-lymphocyte-associated protein 4 (CTLA-4).

BACKGROUND TO THE INVENTION

T-cell exhaustion is a state of T-cell dysfunction that arises during many chronic infections and cancer. It is defined by poor T-cell effector function, sustained expression of inhibitory receptors and a transcriptional state distinct from that of functional effector or memory T-cells. Exhaustion prevents optimal control of infection and tumors. (E John Wherry, *Nature Immunology* 12, 492-499 (2011)).

T-cell exhaustion is characterized by the stepwise and progressive loss of T-cell functions. Exhaustion is well-defined during chronic lymphocytic choriomeningitis virus (LCMV) infection and commonly develops under conditions of antigen-persistence, which occur following many chronic infections including hepatitis B virus, hepatitis C virus and human immunodeficiency virus infections, as well as during tumor metastasis. Exhaustion is not a uniformly disabled setting as a gradation of phenotypic and functional defects can manifest, and these cells are distinct from prototypic effector, memory and also anergic T cells. Exhausted T cells most commonly emerge during high-grade chronic infections, and the levels and duration of antigenic stimulation are critical determinants of the process. (Yi et al., *Immunology* April 2010; 129(4):474-481).

Circulating human tumor-specific CD8$^+$ T cells may be cytotoxic and produce cytokines in vivo, indicating that self- and tumor-specific human CD8$^+$ T cells can reach functional competence after potent immunotherapy such as vaccination with peptide, incomplete Freund's adjuvant (IFA), and CpG or after adoptive transfer. In contrast to peripheral blood, T-cells infiltrating tumor sites are often functionally deficient, with abnormally low cytokine production and upregulation of the inhibitory receptors PD-1, CTLA-4, TIM-3 and LAG-3. Functional deficiency is reversible, since T-cells isolated from melanoma tissue can restore IFN-γ production after short-term in vitro culture. However, it remains to be determined whether this functional impairment involves further molecular pathways, possibly resembling T-cell exhaustion or anergy as defined in animal models. (Baitsch et al., *J Clin Invest.* 2011; 121(6):2350-2360).

Cytotoxic T-lymphocyte-associated protein 4 (CTLA-4), also called CD152, is a type I transmembrane protein encoded in humans by the CTLA4 gene. The molecular properties and biological functions of CTLA-4 described herein are reviewed in McCoy and Le Gros *Immunology* and Cell Biology (1999) 77: 1-10 and Grosso and Kunkel, Cancer Immunity (2013) 13: 5.

Binding of the positive costimulatory receptor CD28 to its ligands CD80 and CD86 on antigen presenting cells (APCs) leads to activation of T cells, resulting in T cell proliferation and production of interleukin-2 (IL-2). CTLA-4 is expressed at the cell surface of activated CD4+ and CD8+ T cells, and is an important negative regulator of T cells function. CTLA-4 has a structure similar to CD28, and also binds to both CD80 and CD86 on APCs, but with greater avidity and affinity (Collins et al., Immunity (2002) 17: 201-210).

CTLA-4 has been shown to negatively regulate immune activation through both intrinsic and extrinsic mechanisms, summarised in Table 1 of Grosso and Kunkel, Cancer Immunity (2013) 13: 5. Briefly, (i) reverse signalling through CD80 and CD86 on APCs results in suppression of T cell responses and/or promotes conversion of naïve T cells to Tregs, (ii) signaling through CTLA-3 stimulates production of regulatory cytokines such as TGF-β, resulting in inhibition of antigen presentation by APCs and inhibition of T cell function, (iii) binding of CTLA-4 to CD80/CD86 reduces availability of these ligands for binding by CD28, resulting in reduced activation of T cells by APCs, (iv) binding of CTLA-4 to CD80/CD86 causes their transendocytosis, reducing the ability for APCs to activate T cells, (v) CTLA-4 recruits inhibitory proteins such as PP2A and PTPN11 to the T cell synapse, inhibiting signalling through CD28 and TCR, (vi) CTLA-4 acts as a high affinity competitor occupying CD80/86 and thereby preventing binding by CD28, (vii) a soluble splice variant of CTLA-4 may be capable of inhibiting T cell activation, and (viii) CTLA-4 inhibits the T cell stop signal, which is important for activation of T cells by APCs.

Inhibition of negative regulation by CTLA-4 has been shown to promote stimulation of adaptive immune response and T cell activation. CTLA-4-blocking antibodies have been shown to be efficacious in mouse models of cancer, and anti-CTLA-4 antibodies such as ipilimumab (Yervoy, MDX-010, 10D1; described in WO2001014424 A1) and tremelimumab (ticilimumab; CP-675,206) are being investigated as strategies to promote anti-tumor immunity in cancer. Blockade of CTLA-4 is also a promising therapeutic strategy for disorders associated with T cell exhaustion such as chronic viral infection.

Ipilimumab has been demonstrated not to be capable of binding to murine CTLA-4 (WO 2001/1014424 A1, Table 5, page 81), and tremelimumab has likewise been shown not to bind to murine CTLA-4 (Hanson et al. Proc Amer Assoc Cancer Res (2004) 64: 877). Hanson et al. also discloses that tremelimumab displays binding to human CD28.

SUMMARY OF THE INVENTION

The present invention is concerned with antibodies, or antigen binding fragments, that bind to CTLA-4. Heavy and light chain polypeptides are also disclosed. The antibodies, antigen binding fragments and polypeptides may be provided in isolated and/or purified form and may be formulated into compositions suitable for use in research, therapy and diagnosis.

In some embodiments the antibody, or antigen binding fragment, or polypeptide may be effective to restore T-cell function in T-cells, e.g. CD4$^+$ or CD8$^+$ T-cells. In some embodiments, the antibody, or antigen binding fragment, or polypeptide may be effective to restore T-cell function in T-cells exhibiting T-cell exhaustion or T-cell anergy.

In one aspect of the present invention an antibody, or antigen binding fragment, is provided, which binds to CTLA-4, and which displays substantially no binding to CD28.

In another aspect of the present invention an antibody, or antigen binding fragment, is provided, which binds to CTLA-4, and which does not prevent or inhibit interaction between CD28 and CD80, and/or interaction between CD28 and CD86.

In one aspect of the present invention an antibody, or antigen binding fragment, is provided, the amino acid sequence of the antibody may comprise the amino acid sequences i) to iii), or the amino acid sequences iv) to vi), or preferably the amino acid sequences i) to vi):

```
        i) LC-CDR1:
                                        (SEQ ID NO: 5)
        RATQGISSWLA;

ii) LC-CDR2:
                                        (SEQ ID NO: 6)
        AASSLQS;

iii) LC-CDR3:
                                        (SEQ ID NO: 7)
        QQANTLPLFT;

iv) HC-CDR1:
                                        (SEQ ID NO: 8)
        SNTAAWN;

v) HC-CDR2:
                                        (SEQ ID NO: 9)
        RTYYRSKWYSDYGLSVKS;

vi) HC-CDR3:
                                        (SEQ ID NO: 10)
        EGSGGTLIY;
``` or a variant thereof in which one or two or three amino acids in one or more of the sequences (i) to (vi) are replaced with another amino acid.

In some embodiments LC-CDR1 is RATQGISSWLA (SEQ ID NO:5). In some embodiments LC-CDR2 is AASSLQS (SEQ ID NO:6). In some embodiments LC-CDR3 is QQANTLPLFT (SEQ ID NO:7). In some embodiments HC-CDR1 is SNTAAWN (SEQ ID NO:8). In some embodiments HC-CDR2 is RTYYRSKWYSDYGLSVKS (SEQ ID NO:9). In some embodiments HC-CDR3 is EGSGGTLIY (SEQ ID NO:10).

In some embodiments the antibody, or antigen binding fragment, may comprise at least one light chain variable region incorporating the following CDRs:

```
        LC-CDR1:
                                        (SEQ ID NO: 5)
        RATQGISSWLA

LC-CDR2:
                                        (SEQ ID NO: 6)
        AASSLQS

LC-CDR3:
                                        (SEQ ID NO: 7)
        QQANTLPLFT.
```

In some embodiments the antibody, or antigen binding fragment, may comprise at least one heavy chain variable region incorporating the following CDRs:

```
        HC-CDR1:
                                        (SEQ ID NO: 8)
        SNTAAWN

HC-CDR2:
                                        (SEQ ID NO: 9)
        RTYYRSKWYSDYGLSVKS

HC-CDR3:
                                        (SEQ ID NO: 10)
        EGSGGTLIY.
```

The antibody may comprise at least one light chain variable region incorporating the CDRs shown in FIG. 1. The antibody may comprise at least one heavy chain variable region incorporating the CDRs shown in FIG. 2.

The antibody may comprise at least one light chain variable region ($V_L$) comprising the amino acid sequence of one of SEQ ID NOs 1, 5, 6, 7; or 2, 5, 6, 7 or one of the amino acid sequences shown in FIG. 1 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 1, 5, 6, 7; or 2, 5, 6, 7, or to the amino acid sequence of the $V_L$ chain amino acid sequence shown in FIG. 1.

The antibody may comprise at least one heavy chain variable region ($V_H$) comprising the amino acid sequence of one of SEQ ID NOs 3, 8, 9, 10; or 4, 8, 9, 10 or one of the amino acid sequences shown in FIG. 2 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 3, 8, 9, 10; or 4, 8, 9, 10, or to the amino acid sequence of the $V_H$ chain amino acid sequence shown in FIG. 2.

The antibody may comprise at least one light chain variable region comprising the amino acid sequence of one of SEQ ID NOs 1, 5, 6, 7; or 2, 5, 6, 7, or one of the amino acid sequences shown in FIG. 1 (or an amino acid sequence having at least 70%, more preferably one of at least 75%, 80%, 85%, 90%, 95%, 96%, 97%, 98%, 99% or 100%, sequence identity to one of SEQ ID NOs 1, 5, 6, 7; or 2, 5, 6, 7, or to one of the amino acid sequences of the $V_L$ chain amino acid sequence shown in FIG. 1) and at least one heavy chain variable region comprising the amino acid sequence of one of SEQ ID NOs 3, 8, 9, 10; or 4, 8, 9, 10, or one of the amino acid sequence shown in FIG. 2 (or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 3, 8, 9, 10; or 4, 8, 9, 10, or to one of the amino acid sequences of the $V_H$ chain amino acid sequence shown in FIG. 2).

The antibody may optionally bind CTLA-4, optionally human or murine CTLA-4. In some embodiments, the antibody is capable of binding to both of human and murine CTLA-4. The antibody may optionally have amino acid sequence components as described above. The antibody may be an IgG. In one embodiment an in vitro complex, optionally isolated, comprising an antibody, or antigen binding fragment, as described herein, bound to CTLA-4 is provided.

The antibody may optionally inhibit or prevent interaction or functional association between human CTLA-4 and human CD80 or CD86, or between murine CTLA-4 and murine CD80 or CD86. Such inhibition or prevention of interaction or functional association between CTLA-4 and CD80 or CD86 may inhibit or prevent CD80 or CD86-mediated activation of CTLA-4, CD80/CTLA-4 signalling or CD86/CTLA-4 signalling.

In one aspect of the present invention an isolated light chain variable region polypeptide is provided, the light chain variable region polypeptide comprising the following CDRs:

```
LC-CDR1:
                                     (SEQ ID NO: 5)
RATQGISSWLA

LC-CDR2:
                                     (SEQ ID NO: 6)
AASSLQS

LC-CDR3:
                                     (SEQ ID NO: 7)
QQANTLPLFT.
```

In one aspect of the present invention an isolated light chain variable region polypeptide is provided, comprising an amino acid sequence having at least 85% sequence identity to the light chain sequence: SEQ ID NO:1 or 2 (FIG. 1). In some embodiments the isolated light chain variable region polypeptide is capable of binding to CTLA-4.

In one aspect of the present invention an isolated heavy chain variable region polypeptide is provided, the heavy chain variable region polypeptide comprising the following CDRs:

```
HC-CDR1:
                                     (SEQ ID NO: 8)
SNTAAWN

HC-CDR2:
                                     (SEQ ID NO: 9)
RTYYRSKWYSDYGLSVKS

HC-CDR3:
                                     (SEQ ID NO: 10)
EGSGGTLIY.
```

In one aspect of the present invention an isolated heavy chain variable region polypeptide is provided, comprising an amino acid sequence having at least 85% sequence identity to the heavy chain sequence of SEQ ID NO:3 or 4 (FIG. 2). In some embodiments the isolated heavy chain variable region polypeptide is capable of binding to CTLA-4.

In one aspect of the present invention an antibody, or antigen binding fragment, is provided, the antibody, or antigen binding fragment, comprising a heavy chain and a light chain variable region sequence, wherein:
the light chain comprises a LC-CDR1, LC-CDR2, LC-CDR3, having at least 85% overall sequence identity to LC-CDR1: RATQGISSWLA (SEQ ID NO:5), LC-CDR2: AASSLQS (SEQ ID NO:6), LC-CDR3: QQANTLPLFT (SEQ ID NO:7), and;
the heavy chain comprises a HC-CDR1, HC-CDR2, HC-CDR3, having at least 85% overall sequence identity to HC-CDR1: SNTAAWN (SEQ ID NO:8), HC-CDR2: RTYYRSKWYSDYGLSVKS (SEQ ID NO:9), HC-CDR3: EGSGGTLIY (SEQ ID NO:10).

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, or antigen binding fragment, optionally isolated, is provided comprising a heavy chain and a light chain variable region sequence, wherein:
the light chain sequence has at least 85% sequence identity to the light chain sequence: SEQ ID NO:1 or 2 (FIG. 1), and;
the heavy chain sequence has at least 85% sequence identity to the heavy chain sequence of SEQ ID NO:3 or 4 (FIG. 2).

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment, or polypeptide further comprises variable region light chain framework sequences between the CDRs according to the arrangement LCFR1:LC-CDR1:LCFR2:LC-CDR2:LCFR3:LC-CDR3:LCFR4. The framework sequences may be derived from human consensus framework sequences.

In one aspect of the present invention an isolated light chain variable region polypeptide, optionally in combination with a heavy chain variable region polypeptide as described herein, is provided, the light chain variable region polypeptide comprising the following CDRs:

```
LC-CDR1:
                                     (SEQ ID NO: 5)
RATQGISSWLA

LC-CDR2:
                                     (SEQ ID NO: 6)
AASSLQS

LC-CDR3:
                                     (SEQ ID NO: 7)
QQANTLPLFT.
```

In some embodiments the antibody, antigen binding fragment, or polypeptide further comprises variable region heavy chain framework sequences between the CDRs according to the arrangement HCFR1:HC-CDR1:HCFR2:HC-CDR2:HCFR3:HC-CDR3:HCFR4. The framework sequences may be derived from human consensus framework sequences.

In one aspect of the present invention an isolated heavy chain variable region polypeptide, optionally in combination with a light chain variable region polypeptide as described herein, is provided, the heavy chain variable region polypeptide comprising the following CDRs:

```
HC-CDR1:
                                     (SEQ ID NO: 8)
SNTAAWN

HC-CDR2:
                                     (SEQ ID NO: 9)
RTYYRSKWYSDYGLSVKS

HC-CDR3:
                                     (SEQ ID NO: 10)
EGSGGTLIY.
```

In some embodiments, the antibody, or antibody binding fragment, may further comprise a human constant region. For example selected from one of IgG1, IgG2, IgG3 and IgG4.

In some embodiments, the antibody, or antibody binding fragment, may further comprise a murine constant region. For example, selected from one of IgG1, IgG2A, IgG2B and IgG3.

In another aspect of the present invention, an antibody or antigen binding fragment, optionally isolated, which is capable of binding to CTLA-4, which is a bispecific antibody or a bispecific antigen binding fragment is provided. The bispecific antibody or antigen binding fragment comprises (i) an antigen binding fragment or polypeptide capable of binding to CTLA-4 as described herein, and (ii) an antigen binding fragment or polypeptide which is capable of binding to a target protein other than CTLA-4.

In some embodiments, the target protein other than CTLA-4 may be a cell surface receptor, e.g. a receptor expressed on the cell surface of T cells. In some embodiments the cell surface receptor may be an immune checkpoint receptor, e.g. a costimulatory receptor or an inhibitory receptor. In some embodiments, the costimulatory receptor may be selected from CD27, CD28, ICOS, CD40, CD122, OX43, 4-1BB and GITR. In some embodiments, the inhibitory receptor may be selected from B7-H3, B7-H4, BTLA, LAG-3, A2AR, VISTA, TIM-3, PD-1, and KIR.

In some embodiments, the target protein other than CTLA-4 may be a cancer marker whose expression is associated with a cancer. In some embodiments, the cancer marker may be expressed at the cell surface. In some embodiments, cancer marker may be selected from HER-2, HER-3, EGFR, EpCAM, CD30, CD33, CD38, CD20, CD24, CD90, CD15, CD52, CA-125, CD34, CA-15-3, CA-19-9, CEA, CD99, CD117, CD31, CD44, CD123, CD133, ABCB5 and CD45.

In another aspect of the present invention a chimeric antigen receptor (CAR) is provided, comprising an antigen binding fragment as described herein.

In another aspect the present invention provides a cell comprising a CAR as described herein.

In another aspect of the present invention an in vitro complex is provided, comprising an antibody, antigen binding fragment, polypeptide, CAR or cell as described herein bound to CTLA-4. The in vitro complex may optionally be isolated.

In another aspect of the present invention, a composition, e.g. a pharmaceutical composition or medicament, is provided. The composition may comprise an antibody, antigen binding fragment, polypeptide, CAR or cell as described herein and at least one pharmaceutically-acceptable carrier, excipient, adjuvant or diluent.

In another aspect of the present invention an isolated nucleic acid encoding an antibody, antigen binding fragment, polypeptide or CAR as described herein is provided. The nucleic acid may have a sequence of one of SEQ ID NOs 11, 12, 13 or 14 (FIG. 3), or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. *E. coli*. In one aspect of the present invention a method for making an antibody, or antigen binding fragment, polypeptide or CAR as described herein is provided, the method comprising culturing a host cell as described herein under conditions suitable for the expression of a vector encoding the antibody, antigen binding fragment, polypeptide or CAR, and recovering the antibody, antigen binding fragment, polypeptide or CAR.

In another aspect of the present invention an antibody, antigen binding fragment, polypeptide, CAR, cell or composition is provided for use in therapy, or in a method of medical treatment. In another aspect of the present invention an antibody, antigen binding fragment, polypeptide, CAR, cell or composition as described herein is provided for use in the treatment of a T-cell dysfunctional disorder. In another aspect of the present invention, the use of an antibody, antigen binding fragment, polypeptide, CAR, cell or composition as described herein in the manufacture of a medicament or pharmaceutical composition for use in the treatment of a T-cell dysfunctional disorder is provided.

In another aspect of the present invention a method of enhancing T-cell function comprising administering an antibody, antigen binding fragment, polypeptide, CAR, cell or composition as described herein to a dysfunctional T-cell is provided. The method may be performed in vitro or in vivo.

In another aspect of the present invention a method of treating a T-cell dysfunctional disorder is provided, the method comprising administering an antibody, antigen binding fragment or polypeptide as described herein to a patient suffering from a T-cell dysfunctional disorder.

In another aspect of the present invention an antibody, antigen binding fragment, polypeptide, CAR, cell or composition is provided for use in the treatment of a cancer. In another aspect of the present invention, the use of an antibody, antigen binding fragment, polypeptide, CAR, cell or composition as described herein in the manufacture of a medicament or pharmaceutical composition for use in the treatment of a cancer is provided.

In another aspect of the present invention a method of killing a tumour cell is provided, the method comprising administering an antibody, antigen binding fragment, polypeptide, CAR, cell or composition as described herein to a tumour cell. The method may be performed in vitro or in vivo. Killing of a tumour cell may, for example, be as a result of antibody dependent cell-mediated cytotoxicity (ADCC), complement dependent cytotoxicity (CDC), or through the action of a drug conjugated to the antibody, antigen binding fragment, polypeptide, CAR, cell or composition.

In another aspect of the present invention a method of treating a cancer is provided, the method comprising administering an antibody, antigen binding fragment, polypeptide, CAR, cell or composition as described herein to a patient suffering from a cancer.

The cancer may be a cancer which expresses or overexpresses CTLA-4, or may comprise cells which express or overexpress CTLA-4.

In another aspect of the present invention a method of modulating an immune response in a subject is provided, the method comprising administering to the subject an antibody, antigen binding fragment, polypeptide, CAR, cell or composition as described herein such that the immune response in the subject is modulated.

In another aspect of the present invention a method of inhibiting growth of tumor cells is provided, comprising administering an antibody, antigen binding fragment, polypeptide, CAR, cell or composition as described herein. The method may be in vitro or in vivo. In some embodiments a method of inhibiting growth of tumor cells in a subject is provided, the method comprising administering to the subject a therapeutically effective amount of an antibody, antigen binding fragment, polypeptide, CAR, cell or composition as described herein.

In another aspect of the present invention a method is provided, the method comprising contacting a sample containing, or suspected to contain, CTLA-4 with an antibody, antigen binding fragment, CAR or cell as described herein, and detecting the formation of a complex of antibody, antigen binding fragment, CAR or cell and CTLA-4.

In another aspect of the present invention a method of diagnosing a disease or condition in a subject is provided, the method comprising contacting, in vitro, a sample from the subject with an antibody, antigen binding fragment, CAR or cell as described herein, and detecting the formation of a complex of antibody, antigen binding fragment, CAR or cell and CTLA-4.

In a further aspect of the present invention the use of an antibody, antigen binding fragment, CAR or cell as described herein, for the detection of CTLA-4 in vitro is provided. In another aspect of the present invention the use of an antibody, antigen binding fragment, CAR or cell as described herein, as an in vitro diagnostic agent is provided.

In methods of the present invention the antibody, antigen binding fragment, polypeptide, CAR or cell may be provided as a composition as described herein.

In another aspect the present invention provides a method of treating or preventing a cancer in a subject, comprising:
(a) isolating at least one cell from a subject;
(b) modifying the at least one cell to express or comprise the antibody, antigen binding fragment, polypeptide, CAR, nucleic acid or vector described herein, and;
(c) administering the modified at least one cell to a subject.

In another aspect the present invention provides a method of treating or preventing a cancer in a subject, comprising:
(a) isolating at least one cell from a subject;
(b) introducing into the at least one cell the nucleic acid or vector described herein, thereby modifying the at least one cell, and;
(c) administering the modified at least one cell to a subject.

In another aspect the present invention provides a kit of parts comprising a predetermined quantity of the antibody, antigen binding fragment, polypeptide, CAR, composition, nucleic acid, vector or cell described herein.

In some embodiments the antibody may be clone 2C8 or 2C8_g1 as described herein.

DESCRIPTION

Antibodies

Antibodies according to the present invention preferably bind to CTLA-4 (the antigen), preferably human or murine CTLA-4, optionally with a $K_D$ in the range 2 to 20 nM.

Antibodies according to the present invention may be provided in isolated form.

Antibodies according to the present invention may exhibit least one of the following properties:
a) binds to human or mouse CTLA-4 with a $K_D$ of 1 μM or less, preferably one of ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 μM (e.g. as determined by SPR);
b) binds to human or mouse CTLA-4 with an affinity of binding of EC50=1 μM or less, preferably one of ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM (e.g. as determined by ELISA);
c) binds to human or mouse CTLA-4 with an avidity of binding of EC50=500 pM or less, preferably one of ≤400 pM, ≤300 pM, ≤200 pM, ≤150 pM, ≤100 pM, ≤90 pM, ≤80 pM, ≤75 pM, ≤70, ≤65 pM, ≤60 pM, ≤55 pM, ≤50 pM (e.g. as determined by ELISA);
d) displays substantially no binding to CD28 (e.g. human CD28 or mouse CD28).
e) binds to human and mouse CTLA-4, and displays substantially no binding to binds to human CD28;
f) inhibits or prevents interaction between CTLA-4 and CD80, optionally human CTLA-4 and human CD80;
g) inhibits or prevents interaction between CTLA-4 and CD86, optionally human CTLA-4 and human CD86;
h) inhibits or prevents interaction between CTLA-4 and CD80 and interaction between CTLA-4 and CD86, optionally human CTLA-4, human CD80 and human CD86;
i) does not inhibit or prevent interaction between CD28 and CD80, optionally human CD28 and human CD80;
j) does not inhibit or prevent interaction between CD28 and CD86, optionally human CD28 and human CD86;
k) does not inhibit or prevent interaction between CD28 and CD80 and interaction between CD28 and CD86, optionally human CD28, human CD80 and human CD86;
l) increases activation of T cells in vitro;
m) increases IL-2 production by T cells in a T cell reactivation assay;
n) increases one or more of T-cell proliferation, IL-2 production and IFNγ production in response to infection;
o) inhibits tumour growth, optionally in vivo.

In some embodiments, the antibody according to the present invention may be useful in methods for expanding a population of immune cells, e.g. T cells. The antibodies according to the invention are useful for expanding populations of immune cells with desirable properties.

In some embodiments, the antibody of the present invention is useful to expand in methods for expanding a population of immune cells with an effector phenotype (e.g. CTLs) in preference to immune cells with an immunoregulatory/immunosuppressive phenotype (e.g. Tregs)

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

In some embodiments, the antibody/fragment is a fully human antibody/fragment. A fully human antibody/fragment is encoded by human nucleic acid sequence(s). Fully human antibodies/fragments are devoid of non-human amino acid sequences.

In some embodiments, the antibody/fragment may be a chimeric antibody/fragment. A chimeric antibody/fragment may comprise amino acid sequences derived from different antibodies/fragments. For example, a chimeric antibody/fragment may comprise CDRs or variable domain sequence(s) from one antibody/antigen binding fragment, and constant region sequence(s) from another antibody/antigen binding fragment. In some embodiments, a chimeric antibody/fragment may comprise CDRs from one antibody/antigen binding fragment, and constant region sequence(s) and framework region sequence(s) from another antibody/antigen binding fragment.

In some embodiments, the chimeric antibody/fragment may comprise CDRs or variable domain sequence(s) of anti-CTLA-4 clone 2C8 or 2C8_gl described herein, and constant region sequence(s) from another antibody/antigen binding fragment. In some embodiments, the chimeric antibody/fragment may comprise CDRs of anti-CTLA-4 clone 2C8 or 2C8_gl described herein, and constant region sequence(s) and framework region sequence(s) from another antibody/antigen binding fragment.

In some embodiments, a chimeric antibody/fragment may comprise CDRs or variable domain sequence(s) from an antibody from one species and constant region sequence(s) from an antibody from another species. In some embodiments, a chimeric antibody/fragment may comprise CDRs from an antibody from one species and constant region sequence(s) and framework region sequence(s) from an antibody from another species.

In some embodiments, a chimeric antibody/fragment according to the present invention may comprise CDRs or variable domain sequence(s) from anti-CTLA-4 clone 2C8 or 2C8_gl described herein, and constant region sequence(s) from an antibody from a non-human species. In some embodiments, a chimeric antibody/fragment according to the present invention may comprise CDRs from anti-CTLA-4 clone 2C8 or 2C8_gl described herein, and constant region sequence(s) and framework region sequence(s) from an antibody from a non-human species. In some embodiments, the non-human species is e.g. a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, or non-human primate).

In some embodiments, an antibody/fragment according to the invention may comprise modifications (e.g. one or more amino acid substitutions) to increase similarity to antibodies naturally produced in a species of interest.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to CTLA-4 may also be made using phage display technology as is well known in the art.

Also provided are multispecific antibodies and multispecific antigen binding fragments, comprising an antigen binding fragment or a polypeptide according to the present invention.

As used herein, 'multispecific' means having specificity for more than one epitope. In some embodiments, a multispecific antibody or multispecific antigen binding fragment may be specific for e.g. 2 (bispecific), 3 (trispecific), 4, 5, 6, 7, 8, 9 or 10 different epitopes.

In some embodiments, multispecific antibodies/fragments according to the invention may have specificity for more than one target molecule. In some embodiments, a multispecific antibody/fragment may be specific for e.g. 2 (bispecific), 3 (trispecific), 4, 5, 6, 7, 8, 9 or 10 different target molecules.

In some embodiments, the multispecific antibodies and multispecific antigen binding fragments comprise an antigen binding fragment capable of binding to CTLA-4, and an antigen binding fragment capable of binding to another target protein. In some embodiments the multispecific antibodies/fragments comprise an antigen binding fragment capable of binding to CTLA-4, and e.g. 1, 2, 3, 4, 5 6, 7, 8, or 9 antigen binding fragment(s) capable of binding to another target protein, i.e. a protein other than CTLA-4.

The present application also provides an antibody or antigen binding fragment which is capable of binding to CTLA-4, and which is a bispecific antibody or a bispecific antigen binding fragment. In some embodiments, the bispecific antibody or bispecific antigen binding fragment may be isolated.

In some embodiments, the bispecific antibodies and bispecific antigen binding fragments comprise an antigen binding fragment or a polypeptide according to the present invention. In some embodiments, the bispecific antibodies and bispecific antigen binding fragments comprise an antigen binding fragment capable of binding to CTLA-4, wherein the antigen binding fragment which is capable of binding to CTLA-4 comprises or consists of an antigen binding fragment or a polypeptide according to the present invention.

In some embodiments the bispecific antibodies and bispecific antigen binding fragments comprise an antigen binding fragment capable of binding to CTLA-4, and an antigen binding fragment capable of binding to another target protein.

The antigen binding fragment capable of binding to another target protein may be capable of binding to another protein other than CTLA-4.

In some embodiments, the target protein may be a cell surface receptor. In some embodiments, the target protein may be a cell surface receptor expressed on the cell surface of an immune cell, e.g. T cell. In some embodiments the cell surface receptor may be an immune checkpoint receptor. In some embodiments, the immune checkpoint receptor may be a costimulatory receptor. In some embodiments, the costimulatory receptor may be selected from CD27, CD28, ICOS, CD40, CD122, OX43, 4-1BB and GITR. In some embodiments, the immune checkpoint receptor may be an inhibitory receptor. In some embodiments, the inhibitory receptor may be selected from B7-H3, B7-H4, BTLA, LAG-3, A2AR, VISTA, TIM-3, PD-1, and KIR.

In some embodiments, the target protein may be a cancer marker. That is, the target protein may be a protein whose expression (e.g. upregulated expression) is associated with a cancer. In some embodiments, the cancer marker may be expressed at the cell surface. In some embodiments the cancer marker may be a receptor. In some embodiments, the cancer marker may be selected from HER-2, HER-3, EGFR, EpCAM, CD30, CD33, CD38, CD20, CD24, CD90, CD15, CD52, CA-125, CD34, CA-15-3, CA-19-9, CEA, CD99, CD117, CD31, CD44, CD123, CD133, ABCB5 and CD45.

In some embodiments, the antigen binding fragment for CD27 may comprise the CDRs, light and heavy chain variable domains or other CD27 binding fragment of e.g. anti-CD27 antibody clone 0323 (Millipore) or varlilumab (Celldex Therapeutics). In some embodiments, the antigen binding fragment for CD28 may comprise the CDRs, light and heavy chain variable domains or other CD28 binding fragment of e.g. anti-CD28 antibody clone CD28.6 (eBioscience), clone CD28.2, clone JJ319 (Novus Biologicals), clone 204.12, clone B-23, clone 10F3 (Thermo Scientific Pierce Antibodies), clone 37407 (R&D Systems), clone 204-12 (Abnova Corporation), clone 15E8 (EMD Millipore), clone 204-12, clone YTH913.12 (AbD Serotec), clone B-T3 (Acris Antibodies), clone 9H6E2 (Sino Biological), clone C28/77 (MyBioSource.com), clone KOLT-2 (ALPCO), clone 152-2E10 (Santa Cruz Biotechnology), or clone XPH-56 (Creative Diagnostics). In some embodiments, the antigen binding fragment for ICOS may comprise the CDRs, light and heavy chain variable domains or other ICOS binding fragment of e.g. anti-ICOS antibody clone ISA-3 (eBioscience), clone SP98 (Novus Biologicals), clone 1G1, clone 3G4 (Abnova Corporation), clone 669222 (R&D Systems), clone TQ09 (Creative Diagnostics), or clone C398.4A (BioLegend). In some embodiments, the antigen binding fragment for CD40 may comprise the CDRs, light and heavy chain variable domains or other CD40 binding fragment of e.g. anti-CD40 antibody clone 82111 (R&D Systems), or ASKP1240 (Okimura et al., AM J Transplant (2014) 14(6) 1290-1299). In some embodiments, the antigen binding fragment for CD122 may comprise the CDRs, light and heavy chain variable domains or other CD122 binding fragment of anti-CD122 antibody clone mikβ2 (PharMingen). In some embodiments, the antigen binding fragment for OX43 may comprise the CDRs, light and heavy chain variable domains or other OX43 binding fragment of e.g. anti-OX43 antibodies disclosed in US 20130280275, U.S. Pat. No. 8,283,450 or WO2013038191, e.g. clone 12H3 or clone 20E5. In some embodiments, the antigen binding fragment for 4-1BB may comprise the CDRs, light and heavy chain variable domains or other 4-1 BB binding fragment of e.g. anti-4-1 BB antibody PF-05082566 (Fisher et al., Cancer Immunol Immunother (2012) 61: 1721-1733), or urelumab (BMS-665513; Bristol-Myers Squibb; Li and Liu, Clin Pharmacol (2013); 5: 47-53). In some embodiments, the antigen binding fragment for GITR may comprise the CDRs, light and heavy chain variable domains or other GITR binding fragment of e.g. anti-GITR antibody TRX-518 (Tolerx®; Schaer et al., (2010) 11(12): 1378-1386), or clone AIT 518D (LifeSpan Biosciences). In some embodiments, the antigen binding fragment for B7-H3 may comprise the CDRs, light and heavy chain variable domains or other B7-H3 binding fragment of e.g. anti-B7-H3 antibody clones disclosed in US 20130078234, WO2014160627 or WO2011109400. In some embodiments, the antigen binding fragment for B7-H4 may comprise the CDRs, light and heavy chain variable domains or other B7-H4 binding fragment of e.g. anti-B7-H4 antibody clones disclosed in WO2013067492, WO2009073533 or EP2934575, for example clone 2H9. In some embodiments, the antigen binding fragment for BTLA may comprise the CDRs, light and heavy chain variable domains or other BTLA binding fragment of e.g. anti-BTLA antibody clone 1B7, clone 2G8, clone 4C5 (Abnova Corporation), clone 4B8 (antibodies-online), clone MIH26 (Thermo Scientific Pierce Antibodies), clone UMAB61 (OriGene Technologies), clone 330104 (R&D Systems), clone 1B4 (LifeSpan BioSciences), clone 440205, clone 5E7 (Creative Diagnostics). In some embodiments, the antigen binding fragment for LAG-3 may comprise the CDRs, light and heavy chain variable domains or other LAG-3 binding fragment of e.g. anti-LAG-3 antibody clone 17B4 (Enzo Life Sciences), clone 333210 (R&D Systems), clone 14L676 (United States Biological), BMS-986016, or an anti-LAG-3 antibody described in WO 2015042246 A1. In some embodiments, the antigen binding fragment for A2AR may comprise the CDRs, light and heavy chain variable domains or other A2AR binding fragment of e.g. anti-A2AR antibody clone 7F6 (Millipore; Koshiba et al. Molecular Pharmacology (1999); 55: 614-624. In some embodiments, the antigen binding fragment for VISTA may comprise the CDRs, light and heavy chain variable domains or other VISTA binding fragment of e.g. anti-VISTA antibodies disclosed in WO2015097536 or US20140105912, e.g. clone 13F3. In some embodiments, the antigen binding fragment for TIM-3 may comprise the CDRs, light and heavy chain variable domains or other TIM-3 binding fragment of e.g. anti-TIM-3 antibody clone F38-2E2 (BioLegend), clone 2E2 (Merck Millipore; Pires da Silva et al., Cancer Immunol Res (2014) 2(5): 410-422), clone 6B6E2, clone 024 (Sino Biological) clone 344801 (R&D Systems), clone E-18, clone H-191 (Santa Cruz Biotechnology), or clone 13A224 (United States Biological). In some embodiments, the antigen binding fragment for PD-1 may comprise the CDRs, light and heavy chain variable domains or other PD-1 binding fragment of e.g. anti-PD-1 antibody clone J116, clone MIH4 (eBioscience), clone 7A11B1 (Rockland Immunochemicals Inc.), clone 192106 (R&D Systems), clone J110, clone J105 (MBL International), clone 12A7D7, clone 7A11B1 (Abbiotec), clone #9X21 (MyBioSource.com), clone 4H4D1 (Proteintech Group), clone D3W4U, clone D3O4S (Cell Signaling Technology), clone RMP1-30, clone RMP1-14 (Merck Millipore), clone EH12.2H7 (BioLegend), clone 10B1227 (United States Biological), clone UMAB198, clone UMAB197 (Origene Technologies), nivolumab (BMS-936558), lambrolizumab, or anti-PD-1 antibodies described in WO 2010/077634 or WO 2006/121168. In some embodiments, the antigen binding fragment for KIR may comprise the CDRs, light and heavy chain variable domains or other KIR binding fragment of e.g. anti-KIR antibody clone 1-7F9 (Romagne et al., Blood (2009) 114(13): 2667-2677), lirilumab (BMS-986015; Sola et al., J Immunother Cancer (2013); 1:P40) or anti-KIR antibodies described in US 2015/0344576 or WO 2014/066532. In some embodiments, the antigen binding fragment for HER-2 may comprise the CDRs, light and heavy chain variable domains or other HER-2 binding fragment of e.g. anti-HER-2 antibody trastuzumab (Herceptin), or anti-HER-2 antibodies described in WO 2003/006509 or WO 2008/019290. In some embodiments, the antigen binding fragment for HER-3 may comprise the CDRs, light and heavy chain variable domains or other HER-3 binding fragment of e.g. anti-HER-3 antibody clone MM-121 (Lyu et al., Int. J Clin Exp Pathol (2015) 8(6): 6143-6156), MEHD7945A (Schaefer et al., Cancer Cell (2011) 20(4): 472-486), AMG 888 (U3-1287; Aurisicchio et al., Oncotarget (2012) 3(8): 744-758) or anti-HER-3 antibodies described in WO2008/100624 or WO 2013048883. In some embodiments, the antigen binding fragment for EGFR may comprise the CDRs, light and heavy chain variable domains or other EGFR binding fragment of e.g. anti-EGFR antibody panitumumab (ABX-EGF; Vectibix), cetuximab (Erbitux), nimotuzumab, matazumab (EMD 7200) or antibody clone 048-006 (Sogawa et al., Nucl Med Comm (2012) 33(7): 719-725). In some embodiments, the antigen binding fragment for EpCAM may comprise the CDRs, light and heavy chain variable domains or other EpCAM binding fragment of e.g. anti-EpCAM antibody edrecolomab, ING-1, 3622W4, or adecatumumab (Munz et al., Cancer Cell Int (2010) 10:44). In some embodiments, the antigen binding fragment for CD30 may comprise the CDRs, light and heavy chain variable domains or other CD30 binding fragment of e.g. anti-CD30 antibody brentuximab (cAC10), clone SGN-30 (Wahl et al., Cancer Res 2002 62(13):3736-3742), clone 5F11 (Borchmann et al., Blood (2003) 102(1): 3737-3742), or anti-CD30 antibodies described in WO 1993024135 or WO 2003059282. In some embodiments, the antigen binding fragment for CD33 may comprise the CDRs, light and heavy chain variable domains or other CD33 binding fragment of e.g. anti-CD33 antibody lintuzumab (SGN-33), gemtuzumab (Mylotarg), or clone hP67.7 (Sievers et al., Blood (1999) 93(11): 3678-3684). In some embodiments, the antigen binding fragment for CD38 may comprise the CDRs, light and heavy chain variable domains or other CD38 binding fragment of e.g. anti-CD38 antibody daratumumab (Darzalex), SAR650984 (Martin et al., J Clin Oncol (2014) 32:5s, (suppl; abstr 8532) or MOR202 (MorphoSys AG), or anti-CD38 antibodies described in WO 2006099875 or US 20100285004. In some embodiments, the antigen binding fragment for CD20 may comprise the CDRs, light and heavy chain variable domains or other CD20 binding fragment of e.g. anti-CD20 antibody rituximab, ocrelizumab, ofatumumab, obinutuzumab or BM-ca (Kobayashi et al., Cancer Med (2013) 2(2): 130-143). In some embodiments, the antigen binding fragment for CD24 may comprise the CDRs, light and heavy chain variable domains or other CD24 binding fragment of e.g. anti-CD24 antibody clone eBioSN3 (eBioscience), clone ML5 (BD Biosciences), or anti-CD24 antibodies described in WO 2008059491. In some embodiments, the antigen binding fragment for CD90 may comprise the CDRs, light and heavy chain variable domains or other CD90 binding fragment of e.g. anti-CD90 antibody clone 5E10 (BD Biosciences). In some embodiments, the antigen binding fragment for CD15 may comprise the CDRs, light and heavy chain variable domains or other CD15 binding fragment of e.g. anti-CD15 antibody clone C3D-1, Carb-3 (DAKO A/S), MMA (Roche) or BY87 (Abcam). In some embodiments, the antigen binding fragment for CD52 may comprise the CDRs, light and heavy chain variable domains or other CD52 binding fragment of e.g. anti-CD52 antibody alemtuzumab, clone HI186, or clone YTH34.5 (AbD Serotec). In some embodiments, the antigen binding fragment for CA-125 may comprise the CDRs, light and heavy chain variable domains or other CA-125 binding fragment of e.g. anti-CA-125 antibody oregovomab. In some embodiments, the antigen binding fragment for CD34 may comprise the CDRs, light and heavy chain variable domains or other CD34 binding fragment of e.g. anti-CD34 antibody clone 561 (BioLegend), clone 581 (Beckton Dickinson), or clone 5F3 (Sigma Aldrich). In some embodiments, the antigen binding fragment for CA-15-3 may comprise the CDRs, light and heavy chain variable domains or other CA-15-3 binding fragment of e.g. anti-CA-15-3 antibody clone 2F16 (USBiological), clone TA998 (ThermoFisher Scientific), clone 1 D1 (Sigma Aldrich), or Mab AR20.5 (Qi et al., Hybrid Hybridomics (2001) 20(5-6): 313-324). In some embodiments, the antigen binding fragment for CA-19-9 may comprise the CDRs, light and heavy chain variable domains or other CA-19-9 binding fragment of e.g. anti-CA-19-9 antibody clone 116-NS-19-9 (DAKO A/S), clone SPM110, or clone 121SLE (ThermoFisher Scientific). In some embodiments, the antigen binding fragment for CEA may comprise the CDRs, light and heavy chain variable domains or other CEA binding fragment of e.g. anti-CEA antibody labetuzumab, C2-45 (Kyowa Hakko Kirin Co. Ltd.) or anti-CEA antibodies disclosed in Imakiire et al., Int J Cancer (2004) 108: 564-570 or WO 2011034660. In some embodiments, the antigen binding fragment for CD99 may comprise the CDRs, light and heavy chain variable domains or other CD99 binding fragment of e.g. anti-CD99 antibody clone C7A (Moricoli et al., J Immunol Methods (2014) 408: 35-45) or clone 12E7 (DAKO A/S). In some embodiments, the antigen binding fragment for CD117 may comprise the CDRs, light and heavy chain variable domains or other CD117 binding fragment of e.g. anti-CD117 antibody clone CK6 (Lebron et al., Cancer Biol Ther (2014) 15(9): 1208-1218), or clone 104D2 (Sigma Aldrich). In some embodiments, the antigen binding fragment for CD31 may comprise the CDRs, light and heavy chain variable domains or other CD31 binding fragment of e.g. anti-CD31 antibody clone JC70A (DAKO A/S). In some embodiments, the antigen binding fragment for CD44 may comprise the CDRs, light and heavy chain variable domains or other CD44 binding fragment of e.g. anti-CD44 antibody PF-03475952 (Runnels et al., Adv Ther (2010); 27(3): 168-180), RG7356 (Vugts et al., MAbs (2014) 6(2): 567-575), clone IM7, or clone A3D8 (Sigma Aldrich). In some embodiments, the antigen binding fragment for CD123 may comprise the CDRs, light and heavy chain variable domains or other CD123 binding fragment of e.g. anti-CD123 antibody CSL362 (Nievergall et al., Blood (2014) 123(8):1218-1228), CSL360 (He et al., Leuk Lymphoma (2015) 56(5): 1406-1415) 73G (Jin et al., Cell Stem Cell (2009) 5(1): 31-42) clone 6H6 (AbD Serotec) or anti-CD123 antibodies described in WO 2014130635. In some embodiments, the antigen binding fragment for CD133 may comprise the CDRs, light and heavy chain variable domains or other CD133 binding fragment of e.g. anti-CD133 antibody clone 6B3, clone 9G4, clone AC141 (Wang et al., Hybridoma (Larchmt) (2010) 29(3): 241-249), clone 6B6 (Chen et al., Hybridoma (Larchmt) (2010) 29(4): 305-310, clone AC113 (Miltenyi Biotec), or anti-CD133 antibodies described in WO 2011149493. In some embodiments, the antigen binding fragment for ABCB5 may comprise the CDRs, light and heavy chain variable domains or other ABCB5 binding fragment of e.g. anti-ABCB5 antibody clone 5H3C6

(Thermo Fisher Scientific). In some embodiments, the antigen binding fragment for CD45 may comprise the CDRs, light and heavy chain variable domains or other CD45 binding fragment of e.g. anti-CD45 antibody YAML568 (Glatting et al., J Nucl Med (2006) 47(8): 1335-1341) or clone BRA-55 (Sigma Aldrich).

An antigen binding fragment of a bispecific antibody or bispecific antigen binding fragment according to the present invention may be any fragment of a polypeptide which is capable of binding to an antigen. In some embodiments, an antigen binding fragment comprises at least the three light chain CDRs (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

Bispecific antibodies and bispecific antigen binding fragments according to the invention may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

The skilled person is able to design and prepare bispecific antibodies and bispecific antigen binding fragments according to the present invention.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Färber-Schwarz), or French, How to make bispecific antibodies, Methods Mol. Med. 2000; 40:333-339, the entire contents of both of which are hereby incorporated by reference. For example, a DNA construct encoding the light and heavy chain variable domains for the two antigen binding fragments (i.e. the light and heavy chain variable domains for the antigen binding fragment capable of binding CTLA-4, and the light and heavy chain variable domains for the antigen binding fragment capable of binding to another target protein), and including sequences encoding a suitable linker or dimerization domain between the antigen binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. Gene 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention preferably exhibit specific binding to CTLA-4. An antibody that specifically binds to a target molecule preferably binds the target with greater affinity, and/or with greater duration than it binds to other targets. In some embodiments the present antibodies may bind with greater affinity to CTLA-4 than to one or more of PD-1, TIM-3, ICOS, BTLA, CD28 or LAG-3.

In embodiments of the present invention, the antibody, fragment or polypeptide displays substantially no binding to CD28, e.g. human CD28. This is an unexpected feature for an antibody capable of binding to CTLA-4, because prior art antibodies (e.g. antibody clone L3D10) display binding to CD28 at high concentrations (see e.g. FIG. 5). Advantageously, such antibodies are able to inhibit/prevent CTLA-4/CD80 or CTLA-4/CD86 signalling, without inhibiting/preventing CD28/CD80 or CD28/CD86 signalling.

'Substantially no binding' as used herein refers to binding which is not significantly greater than the level of binding by a negative control antibody (e.g. an antibody directed against a target unrelated to CD28, or an antibody known not to bind to CD28). In some embodiments, an antibody according to the present invention may exhibit binding to CD28 (e.g. human CD28) which is ≤500%, ≤400%, ≤300%, ≤250%, ≤200%, ≤150%, or ≤100% of the binding to CD28 displayed by a negative control antibody (e.g. an antibody directed against a target unrelated to CD28, or an antibody known not to bind to CD28), in a given assay or at a given concentration.

Binding of an antibody according to the present invention to a given molecule can be measured by techniques well known to the person skilled in the art, including ELISA, SPR, Bio-Layer Interferometry, flow cytometry or by a radioimmunoassay (RIA). Through such analysis binding to a given target can be measured and quantified. In some embodiments, the binding may be the response detected in a given assay.

In one embodiment, the extent of binding of an antibody to an unrelated target is less than about 10% of the binding of the antibody to the target as measured, e.g., by ELISA, SPR, Bio-Layer Interferometry or by RIA. Alternatively, the binding specificity may be reflected in terms of binding affinity where the anti-CTLA-4 antibody of the present invention binds to CTLA-4 with a $K_D$ that is at least 0.1 order of magnitude (i.e. $0.1 \times 10^n$, where n is an integer representing the order of magnitude) greater than the $K_D$ of the antibody towards another target molecule. This may optionally be one of at least 0.2, 0.3, 0.4, 0.5, 0.6, 0.7, 0.8, 0.9, 1.0, 1.5, or 2.0.

Antibodies according to the present invention preferably have a dissociation constant ($K_D$) of one of ≤10 nM, ≤5 nM, ≤3 nM, ≤2 nM, ≤1.5 nM, ≤1.4 nM, ≤1.3 nM, ≤1.25 nM, ≤1.24 nM, ≤1.23 nM, ≤1.22 nM, ≤1.21 nM, ≤1.2 nM, ≤1.15 nM, ≤1.1 nM, ≤1.05 nM, ≤1 nM, ≤900 μM, ≤800 μM, ≤700 μM, ≤600 μM, ≤500 μM. The $K_D$ may be in the range about 0.1 to about 3 nM. Binding affinity of an antibody for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), or by a radiolabeled antigen binding assay (RIA) performed with the Fab version of the antibody and antigen molecule.

Antibodies according to the present invention preferably exhibit binding to CTLA-4 (e.g. human CTLA-4 or mouse CTLA-4) with greater affinity than, or with similar affinity to, affinity of binding by a reference anti-CTLA-4 antibody. Relative affinity of binding of an antibody according to the invention and a reference antibody to a given target can be determined for example by ELISA, as described herein.

Antibodies according to the invention may exhibit binding to human CTLA-4 with greater affinity than, or with similar affinity to, affinity of binding by antibody clone L3D10 (described, for example, in May et al., Blood (2005) 105: 1114-1120). In some embodiments, the antibodies may exhibit binding to mouse CTLA-4 with greater affinity than, or with similar affinity to, a reference antibody capable of binding to mouse CTLA-4.

As used herein, an antibody displaying 'greater affinity' for a given target molecule compared to a reference antibody binds to that target molecule with greater strength as compared to the strength of binding of the reference antibody to the target molecule. The affinity of an antibody for a given target molecule can be determined quantitatively. In some embodiments, an antibody displaying greater affinity than a reference antibody for a target protein may bind to the target molecule with a $K_D$ value or an EC50 value which is less than the value for binding of that target by the reference antibody.

In some embodiments, an antibody according to the present invention may have affinity for CTLA-4 which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than the affinity of a reference antibody for CTLA-4, in a given assay. In some embodiments, an antibody to according to the present invention may bind to CTLA-4 with a $K_D$ value or EC50 value which is 0.99 times or less, 0.95 times or less, 0.9 times or less, 0.85 times or less, 0.8 times or less, 0.75 times or less, 0.7 times or less, 0.65 times or less, 0.6 times or less, 0.55 times or less, 0.5 times or less of the corresponding $K_D$ value or EC50 value of a reference antibody for CTLA-4, in a given assay.

Antibodies according to the present invention preferably bind to human or mouse CTLA-4 with an avidity of binding of EC50=500 pM or less, preferably one of ≤400 pM, ≤300 pM, ≤200 pM, ≤150 pM, ≤100 pM, ≤90 pM, ≤80 pM, ≤75 pM, ≤70, ≤65 pM, ≤60 pM, ≤55 pM, ≤50 pM. As used herein, avidity of binding refers to the strength of binding of an antibody to a target molecule to form an antibody:target complex. An antibody binding with high avidity binds to a target molecule more strongly, and therefore forms a stable antibody:target complex. Avidity of binding of an antibody to a target molecule can be analysed by ELISA, e.g. as described herein, and quantified.

In some embodiments, an antibody according to the invention may inhibit/prevent interaction between CTLA-4 and CD80. In some embodiments, an antibody according to the invention may inhibit/prevent interaction between CTLA-4 and CD86. In some embodiments, an antibody according to the invention may inhibit/prevent interaction between CTLA-4 and CD80, and inhibit/prevent interaction between CTLA-4 and CD86.

Inhibition/prevention of interaction between CTLA-4 and CD80 or CD86 may be inferred by analysis of a response associated with interaction between CTLA-4 and CD80 or CD86. Relative inhibition/prevention of interaction between CTLA-4 and CD80 or CD86 of an antibody according to the invention can be determined in vitro for example as described herein.

In some embodiments, an antibody according to the present invention may inhibit/prevent interaction between CTLA-4 and CD80 or CD86 to an extent which is greater than or equal to inhibition/prevention of interaction between CTLA-4 and CD80 or CD86 by a reference antibody capable of binding to CTLA-4, e.g. antibody clone L3D10. In some embodiments, an antibody according to the present invention may inhibit/prevent interaction between CTLA-4 and CD80 or CD86 to an extent which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than inhibition/prevention of interaction between CTLA-4 and CD80 or CD86 by a reference antibody capable of binding to CTLA-4, in a given assay.

In some embodiments, an antibody according to the invention may not inhibit/prevent interaction between CD28 and CD80. In some embodiments, an antibody according to the invention may not inhibit/prevent interaction between CD28 and CD86. In some embodiments, an antibody according to the invention may not inhibit/prevent interaction between CD28 and CD80, and may not inhibit/prevent interaction between CD28 and CD86.

Inhibition/prevention of interaction between CD28 and CD80 or CD86 may be analysed by measuring a response associated with interaction between CD28 and CD80 or CD86, e.g. in an in vitro assay.

In some embodiments, in the presence of an antibody according to the present invention a response associated with interaction between CD28 and CD80 or CD86 may be ≥70%, ≥75%, ≥80%, ≥85%, ≥90%, ≥95%, or ≥99% of the response in the absence of the antibody, or the response in the presence of a negative control antibody (i.e. an antibody which directed against an unrelated target, or an antibody known not to bind to CD28, CD80 or CD86).

In some embodiments, an antibody according to the present invention may inhibit/prevent interaction between CTLA-4 and CD80 or CD86 to an extent which is greater than or equal to inhibition/prevention of interaction between CTLA-4 and CD80 or CD86 by a reference antibody capable of binding to CTLA-4, e.g. antibody clone L3D10. In some embodiments, an antibody according to the present invention may inhibit/prevent interaction between CTLA-4 and CD80 or CD86 to an extent which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than inhibition/prevention of interaction between CTLA-4 and CD80 or CD86 by a reference antibody capable of binding to CTLA-4, in a given assay.

Antibodies according to the present invention preferably increase activation of T cells in vitro. Increased activation of T cells may be inferred by detection of one or more of increased T-cell proliferation, IL-2 expression/production, or IFNγ expression/production by T cells, in a given assay. T cell proliferation may be evaluated by methods well known to the skilled person, such as by measuring incorporation of tritiated thymidine or by CFSE dye dilution, e.g. as described in Anthony et al., 2012 Cells 1:127-140. IL-2 and/or IFNγ expression/production may be analysed e.g. nucleic acid and/or antibody-based methods well known to the skilled person, such as qRT-PCR, western blot, immunohistochemistry, immunocytochemistry, flow cytometry, ELISA, ELISPOT, or by reporter-based methods.

In some embodiments, an antibody according to the present invention may increase one or more of T-cell proliferation, IL-2 production and IFNγ production to a similar extent to, or to a greater extent than, a reference antibody capable of binding to CTLA-4 (e.g. L3D10) in a given assay. In some embodiments, an antibody according to the present invention may increase one or more of T-cell proliferation, IL-2 production and IFNγ production to an extent which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than increase in T-cell proliferation, IL-2 production and IFNγ production in response to a reference antibody capable of binding to CTLA-4, in a given assay.

In some embodiments, an antibody according to the invention may be capable of inhibiting tumour growth or cancer progression. In some embodiments an antibody according to the invention may display anti-cancer activity. In some embodiments, inhibition of tumour growth or cancer progression may be in vivo. 'Inhibition' may be reduction or control of tumour growth, or reduction or control of the number of cancer cells. Inhibition of tumour growth or cancer progression can be evaluated in vivo, for example in an animal model of a cancer as described herein.

Antibodies according to the present invention may be "antagonist" antibodies that inhibit or reduce a biological activity of the antigen to which it binds. Blocking of interaction between CTLA-4 and CD80 and/or CD86 assists in the restoration of T-cell function by inhibiting the immune-inhibitory signalling pathway mediated by CTLA-4.

The present invention also provides a chimeric antigen receptor (CAR) comprising an antigen binding fragment according to the present invention.

Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety.

CARs comprise an antigen-binding region linked to a cell membrane anchor region and a signaling region. An optional hinge region may provide separation between the antigen-binding region and cell membrane anchor region, and may act as a flexible linker.

The antigen-binding region of a CAR may be based on the antigen-binding region of an antibody which is specific for the antigen to which the CAR is targeted, or other agent capable of binding to the target. For example, the antigen-binding domain of a CAR may comprise amino acid sequences for the complementarity-determining regions (CDRs) or complete light chain and heavy chain variable region amino acid sequences of an antibody which binds specifically to the target protein. Antigen-binding domains of CARs may target antigen based on other protein:protein interaction, such as ligand:receptor binding; for example an IL-13Rα2-targeted CAR has been developed using an antigen-binding domain based on IL-13 (see e.g. Kahlon et al. 2004 Cancer Res 64(24): 9160-9166).

The CAR of the present invention comprises a CTLA-4 binding region. In some embodiments, the CAR of the present invention comprises an antigen binding region which comprises or consists of an antibody/antigen binding fragment according to the present invention.

The CTLA-4 binding region of the CAR of the present invention may be provided with any suitable format, e.g. scFv, Fab, etc. In some embodiments, the CTLA-4 binding region of the CAR of the present invention comprises or consists of a CTLA-4 binding scFv.

The cell membrane anchor region is provided between the antigen-binding region and the signalling region of the CAR. The cell membrane anchor region provides for anchoring the CAR to the cell membrane of a cell expressing a CAR, with the antigen-binding region in the extracellular space, and signalling region inside the cell. In some embodiments, the CAR of the present invention comprises a cell membrane anchor region comprising or consisting of an amino acid sequence which comprises, consists of, or is derived from, the transmembrane region amino acid sequence for one of CD3-ζ, CD4, CD8 or CD28.

As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins have also been employed in CARs, such as domains comprising the ITAM containing region of FcγRI (Haynes et al., 2001 J Immunol 166(1):182-187). CARs comprising a signalling region derived from the intracellular domain of CD3-ζ, are often referred to as first generation CARs.

Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1BB, ICOS and CD27. CARs having a signalling region including additional co-stimulatory sequences are often referred to as second generation CARs.

In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1 BB-mediated signalling is through TNF receptor associated factor (TRAF) adaptor proteins. Signalling regions of CARs therefore sometimes contain co-stimulatory sequences derived from signalling regions of more than one co-stimulatory molecule. CARs comprising a signalling region with multiple co-stimulatory sequences are often referred to as third generation CARs.

In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be flexible domains allowing the binding moiety to orient in different directions. Hinge regions may be derived from IgG1 or the CH2CH3 region of immunoglobulin. In some embodiments, the CAR of the present invention comprises a hinge region comprising or consisting of an amino acid sequence which comprises, consists of, or is derived from, the amino acid sequence of the hinge region of IgG1 or the CH2CH3 region of immunoglobulin.

CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi: 10.1158/2159-8290.CD-12-0548, specifically incorporated herein by reference).

Also provided is a cell comprising a CAR according to the invention. The CAR according to the present invention may be used to generate T cells. Engineering of CARs into T cells may be performed during culture, in vitro, for transduction and expansion, such as happens during expansion of T cells for adoptive T cell therapy.

In some aspects, the antibody is clone 2C8 or 2C8_gl, or a variant of 2C8 or 2C8_gl. 2C8 and 2C8_gl comprise the following CDR sequences:

```
LC-CDR1:
                           (SEQ ID NO: 5)
RATQGISSWLA

LC-CDR2:
                           (SEQ ID NO: 6)
AASSLQS

LC-CDR3:
                           (SEQ ID NO: 7)
QQANTLPLFT.
```

Heavy Chain:

```
HC-CDR1:
                           (SEQ ID NO: 8)
SNTAAWN
```

-continued
```
HC-CDR2:
                           (SEQ ID NO: 9)
RTYYRSKWYSDYGLSVKS

HC-CDR3:
                           (SEQ ID NO: 10)
EGSGGTLIY.
```

CDR sequences determined by Kabat definition.

Antibodies according to the present invention may comprise the CDRs of 2C8 or 2C8_gl or one of SEQ ID NOs 1 and 3; or 2 and 4. In an antibody according to the present invention one or two or three or four of the six CDR sequences may vary. A variant may have one or two amino acid substitutions in one or two of the six CDR sequences.

Amino acid sequences of the $V_H$ and $V_L$ chains of anti-CTLA-4 clones are shown in FIGS. 1 and 2. The encoding nucleotide sequences are shown in FIG. 3.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Lefranc (2001) "The Immunoglobulin Facts-Book", Academic Press, incorporated herein by reference.

In this specification, antibodies may have $V_H$ and/or $V_L$ chains comprising an amino acid sequence that has a high percentage sequence identity to one or more of the $V_H$ and/or $V_L$ amino acid sequences of SEQ ID NOs 1 and 3; or 2 and 4, or to one or the amino acid sequences shown in FIGS. 1 and 2.

For example, antibodies according to the present invention include antibodies that bind CTLA-4 and have a $V_H$ or $V_L$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_H$ or $V_L$ chain amino acid sequence of one of SEQ ID NOs 1 to 4, or to one or the amino acid sequences shown in FIGS. 1 and 2.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabeled antibody which can be detected by another antibody which is itself labelled. Alternatively, the second antibody may have bound to it biotin and binding of labelled streptavidin to the biotin is used to indirectly label the first antibody.

Nucleic Acids/Vectors

The present invention provides a nucleic acid encoding an antibody, antigen binding fragment or CAR according to the present invention. In some embodiments, the nucleic acid is purified or isolated, e.g. from other nucleic acid, or naturally-occurring biological material.

The present invention also provides a vector comprising nucleic acid encoding an antibody, antigen binding fragment or CAR according to the present invention.

The nucleic acid and/or vector according to the present invention may be provided for introduction into a cell, e.g. a primary human immune cell. Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes), e.g. as described in Maus et al., Annu Rev Immunol (2014) 32:189-225 or Morgan and Boyerinas, Biomedicines 2016 4, 9, which are both hereby incorporated by reference in its entirety. In some embodiments, the viral vector may be a lentiviral, retroviral, adenoviral, or Herpes Simplex Virus vector. In some embodiments, the lentiviral vector may be pELNS, or may be derived from pELNS. In some embodiments, the vector may be a vector encoding CRISPR/Cas9.

Cells Comprising/Expressing the Antibodies/Fragments/CARs

The present invention also provides a cell comprising or expressing an antibody, antigen binding fragment or CAR, according to the present invention. Also provided is a cell comprising or expressing a nucleic acid or vector according to the invention.

The cell may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell may be from, or may have been obtained from, a human subject.

The cell may be an immune cell. The cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ξ, or CD3δ), TCR polypeptides (TCRα or TCRβ), CD27, CD28, CD4 or CD8. In some embodiments, the cell is a T cell. In some embodiments, the T cell is a CD3+ T cell. In some embodiments, the T cell is a CD3+, CD8+ T cell. In some embodiments, the T cell is a cytotoxic T cell (e.g. a cytotoxic T lymphocyte (CTL)).

Where the cell is a T cell comprising a CAR according to the present invention, the cell may be referred to as a CAR-T cell.

In some embodiments, the cell is an antigen-specific T cell. In embodiments herein, a "antigen-specific" T cell is a cell which displays certain functional properties of a T cell in response to the antigen for which the T cell is specific, or a cell expressing said antigen. In some embodiments, the properties are functional properties associated with effector T cells, e.g. cytotoxic T cells. In some embodiments, an antigen-specific T cell may display one or more of the following properties: cytotoxicity, e.g. to a cell comprising/expressing antigen for which the T cell is specific; proliferation, IFNγ expression, CD107a expression, IL-2 expression, TNFα expression, perforin expression, granzyme expression, granulysin expression, and/or FAS ligand (FASL) expression, e.g. in response to antigen for which the T cell is specific or a cell comprising/expressing antigen for which the T cell is specific. In some embodiments, the antigen for which the T cell is specific may be a peptide or polypeptide of a virus, e.g. Epstein-Barr virus (EBV), influenza virus, measles virus, hepatitis B virus (HBV), hepatitis C virus (HCV), human immunodeficiency virus (HIV), lymphocytic choriomeningitis virus (LCMV), Herpes simplex virus (HSV) or human papilloma virus (HPV).

The present invention also provides a method for producing a cell comprising a nucleic acid or vector according to the present invention, comprising introducing a nucleic acid or vector according to the present invention into a cell. The present invention also provides a method for producing a cell expressing an antibody, antigen binding fragment or CAR, according to the present invention, comprising introducing a nucleic acid or vector according to the present invention in a cell. In some embodiments, the methods additionally comprise culturing the cell under conditions suitable for expression of the nucleic acid or vector by the cell. In some embodiments, the methods are performed in vitro.

In some embodiments, introducing an isolated nucleic acid or vector according to the invention into a cell comprises transduction, e.g. retroviral transduction. Accordingly, in some embodiments the isolated nucleic acid or vector is comprised in a viral vector, or the vector is a viral vector. In some embodiments, the method comprises introducing a nucleic acid or vector according to the invention by electroporation, e.g. as described in Koh et al., Molecular Therapy—Nucleic Acids (2013) 2, e114, which is hereby incorporated by reference in its entirety.

The present invention also provides cells obtained or obtainable by the methods for producing a cell according to the present invention.

Methods of Detection

Antibodies, antigen binding fragments, CARs or cells described herein may be used in methods that involve the binding of the antibody, antigen binding fragment, CAR or cell to CTLA-4. Such methods may involve detection of the bound complex of antibody, antigen binding fragment, CAR or cell and CTLA-4. As such, in one embodiment a method is provided, the method comprising contacting a sample containing, or suspected to contain, CTLA-4 with an antibody, antigen binding fragment, CAR or cell as described herein and detecting the formation of a complex of antibody, antigen binding fragment, CAR or cell and CTLA-4.

Suitable method formats are well known in the art, including immunoassays such as sandwich assays, e.g. ELISA. The method may involve labelling the antibody, antigen binding fragment, CAR or cell, or CTLA-4, or both, with a detectable label, e.g. fluorescent, luminescent or radio-label. CTLA-4 expression may be measured by immunohistochemistry (IHC), for example of a tissue sample obtained by biopsy.

Methods of this kind may provide the basis of a method of diagnosis of a disease or condition requiring detection and or quantitation of CTLA-4 or CD80 or CD86. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of CTLA-4 present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

Cancer cells may exploit the CTLA-4 pathway to create an immunosuppressive environment, by upregulating expression of CTLA-4, allowing activation of the inhibitory CTLA-4 receptor on any T cells that infiltrate the tumor microenvironment and thereby suppressing their activity. Upregulation of CTLA-4 expression has been demonstrated in many different cancer types, and high CTLA-4 expression has also been linked to poor clinical outcomes.

The level of CTLA-4 or CD80 or CD86 present in a patient sample may be indicative that a patient may respond to treatment with an anti-CTLA-4 antibody. The presence of a high level of CTLA-4 or CD80 or CD86 in a sample may be used to select a patient for treatment with an anti-CTLA-4 antibody. The antibodies of the present invention may therefore be used to select a patient for treatment with anti-CTLA-4 therapy.

Detection in a sample of CTLA-4 may be used for the purpose of diagnosis of a T-cell dysfunctional disorder or a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

In one embodiment the level of CTLA-4 expression on CD8+ T cells may be detected in order to indicate the degree of T-cell exhaustion and severity of the disease state.

In one embodiment the level of CD80 or CD86 expression, e.g. on antigen presenting cells or tumor cells, may be detected in order to indicate existence or severity of a disease state, for example infection, tissue inflammation or a cancer.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

Therapeutic Applications

Antibodies, antigen binding fragments, CARs, cells and polypeptides according to the present invention and compositions comprising such agents may be provided for use in methods of medical treatment. Treatment may be provided to subjects having a disease or condition in need of treatment. The disease or condition may be one of a T-cell dysfunctional disorder, including a T-cell dysfunctional disorder associated with a cancer, or a cancer, or a T-cell dysfunctional disorder associated with an infection, or an infection.

A T-cell dysfunctional disorder may be a disease or condition in which normal T-cell function is impaired causing downregulation of the subject's immune response to pathogenic antigens, e.g. generated by infection by exogenous agents such as microorganisms, bacteria and viruses, or generated by the host in some disease states such as in some forms of cancer (e.g. in the form of tumor associated antigens).

The T-cell dysfunctional disorder may comprise T-cell exhaustion or T-cell anergy. T-cell exhaustion comprises a state in which $CD8^+$ T-cells fail to proliferate or exert T-cell effector functions such as cytotoxicity and cytokine (e.g. IFNγ) secretion in response to antigen stimulation. Exhausted T-cells may also be characterised by sustained expression of CTLA-4, where blockade of CTLA-4:CD80 or CTLA-4:CD86 interactions may reverse the T-cell exhaustion and restore antigen-specific T cell responses.

The T-cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*. Examples of viral infections include infection with HIV, hepatitis B or hepatitis C.

The T-cell dysfunctional disorder may be associated with a cancer, such as tumor immune escape. Many human tumors express tumor-associated antigens recognised by T cells and capable of inducing an immune response. Inhibition of negative regulation of T cell activation through CTLA-4 has been shown to be a promising treatment for cancers in several studies, reviewed for example in Grosso and Kunkel, Cancer Immunity (2013) 13: 5.

Cancers may also be treated where there is no indication of a T-cell dysfunctional disorder such as T-cell exhaustion but the use of an antibody, antigen binding fragment, polypeptide, CAR or cell according to the present invention allows the subject to suppress CTLA-4 signalling and mount an effective immune response with limited impairment, evasion or induction of tumor immune escape. In such treatments, the antibody, antigen binding fragment, polypeptide, CAR or cell may provide a treatment for cancer that involves prevention of the development of tumor immune escape.

Cancers may also be treated which overexpress CTLA-4. For example, such tumor cells overexpressing CTLA-4 may be killed directly by treatment with anti-CTLA-4 antibodies, by antibody dependent cell-mediated cytotoxicity (ADCC), complement dependent cytotoxicity (CDC), or using anti-CTLA-4 antibody-drug conjugates.

The treatment may be aimed at prevention of the T-cell dysfunctional disorder, e.g. prevention of infection or of the development or progression of a cancer. As such, the antibodies, antigen binding fragments, CARs, cells and polypeptides may be used to formulate pharmaceutical compositions or medicaments and subjects may be prophylactically treated against development of a disease state. This may take place before the onset of symptoms of the disease state, and/or may be given to subjects considered to be at greater risk of infection or development of cancer.

Treatment may comprise co-therapy with a vaccine, e.g. T-cell vaccine, which may involve simultaneous, separate or sequential therapy, or combined administration of vaccine and antibody, antigen binding fragment, CAR, cell or polypeptide in a single composition. In this context, the antibody, antigen binding fragment, CAR, cell or polypeptide may be provided as an adjuvant to the vaccine. Limited proliferative potential of exhausted T cells has been attributed as a main reason for failure of T-cell immunotherapy, and the combination of an agent capable of blocking or reversing T cell exhaustion is a potential strategy for improving the efficacy of T-cell immunotherapy (Barber et al., *Nature* Vol 439, No. 9 p 682-687 February 2006).

Administration of an antibody, antigen binding fragment, CAR, cell or polypeptide is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies, antigen binding fragments, CARs, cells and polypeptides according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment, CAR, cell or polypeptide as described herein; and/or mixing an isolated antibody, antigen binding fragment, CAR, cell or polypeptide as described herein with a pharmaceutically acceptable carrier, adjuvant, excipient or diluent.

For example, a further aspect of the present invention relates to a method of formulating or producing a medicament or pharmaceutical composition for use in the treatment of a T-cell dysfunctional disorder, the method comprising formulating a pharmaceutical composition or medicament by mixing an antibody, antigen binding fragment, CAR, cell or polypeptide as described herein with a pharmaceutically acceptable carrier, adjuvant, excipient or diluent.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry *Nature Immunology* Vol. 12, No. 6, p 492-499, June 2011).

An infection or infectious disease may be one in which CTLA-4 is upregulated.

Examples of bacterial infections that may be treated include infection by *Bacillus* spp., *Bordetella pertussis*, *Clostridium* spp., *Corynebacterium* spp., *Vibrio cholerae*, *Staphylococcus* spp., *Streptococcus* spp. *Escherichia, Klebsiella, Proteus, Yersinia, Erwina, Salmonella, Listeria* sp, *Helicobacter pylori*, mycobacteria (e.g. *Mycobacterium tuberculosis*) and *Pseudomonas aeruginosa*. For example, the bacterial infection may be sepsis or tuberculosis.

Kirman et al., Infect Immun (1999) 67(8): 3786-3792 describes ability of CTLA-4 blockade to enhance the immune response induced by mycobacterial infection, and Rowe et al., Immunology (2008) 128: e471-e478 describes augmentation of the T cell response to infection by *Listeria monocytogenes* by blockade of CTLA-4.

Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

During HIV infection, expression of CTLA-4 has been shown to be positively correlated with virus load, and CTLA-4 blockade has been shown to restore proliferation of HIV-specific CD4+ T-cells and production of IFN-γ and IL-2 (Kaufmann et al. Nat Immunol (2007) 8:1246-1252). Blockade of CTLA-4 also decreases the production by HIV-specific CD8+ T cells of TGF-β and IL-10, but increases production of IFN-γ production by HIV-specific CD8+ T cells (Elrefaei et al. PLoS One (2009) 4(12): e8194).

Chronic viral infections, such as those caused by LCMV, HCV, HBV, and HIV commonly involve mechanisms to evade immune clearance, such as increased expression of inhibitory receptors. Schurich et al. (2011) 53(5): 1494-1503 describes upregulated expression of CTLA-4 on CD8 T cells in patients with chronic HBV infection, and that this correlates with viral load.

Examples of fungal infections that may be treated include infection by *Alternaria* sp, *Aspergillus* sp, *Candida* sp and *Histoplasma* sp. The fungal infection may be fungal sepsis or histoplasmosis. The importance of T cell exhaustion in mediating fungal infection has been established e.g. by Chang et al. Critical Care (2013) 17:R85, and Lázár-Molnár et al PNAS (2008) 105(7): 2658-2663.

Examples of parasitic infections that may be treated include infection by *Plasmodium* species (e.g. *Plasmodium falciparum, Plasmodium yoeli, Plasmodium ovale, Plasmodium vivax*, or *Plasmodium chabaudi chabaudi*). The parasitic infection may be a disease such as malaria, leishmaniasis and toxoplasmosis.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

In some embodiments, the cancer to be treated may be a cancer of a tissue selected from the group consisting of colon, rectum, nasopharynx, cervix, oropharynx, stomach, liver, head and neck, oral cavity, oesophagus, lip, mouth, tongue, tonsil, nose, throat, salivary gland, sinus, pharynx, larynx, prostate, lung, bladder, skin, kidney, ovary or mesothelium.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In particular embodiments, the cancer to be treated may be prostate cancer, small cell lung cancer, non-small cell lung cancer, bladder cancer or melanoma (e.g. advanced melanoma).

In some embodiments, the cancer to be treated may be colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer or mesothelioma.

Adoptive T Cell Transfer Therapy

In embodiments of the present invention, a method of treatment or prophylaxis may comprise adoptive cell transfer of immune cells. Adoptive T cell transfer therapy generally refers to a process in which white blood cells are removed from a subject, typically by drawing a blood sample from which white blood cells are separated, expanded in vitro or ex vivo and returned either to the same subject or to a different subject. The treatment is typically aimed at increasing the amount/concentration of an active form of the required T cell population in the subject. Such treatment may be beneficial in subjects experiencing T cell exhaustion.

Antibodies capable of blocking the mechanism of T cell exhaustion, or reversing it, provide a means of enhancing T cell activity and promoting T cell expansion.

Antibodies directed against immune checkpoint receptors (such as CTLA-4) can also be useful in methods of T cell expansion, e.g. for expanding T cell populations of particular interest. For example, antibodies may be useful in methods of T cell expansion for preferentially expanding T cell subsets having desirable properties (e.g. in preference to T cell subsets having undesirable properties).

Accordingly, in a further aspect of the present invention a method is provided for expanding a population of T cells, wherein T cells are contacted in vitro or ex vivo with an antibody, antigen binding fragment, CAR, cell or polypeptide according to the present invention.

The method may optionally comprise one or more of the following steps: taking a blood sample from a subject; isolating T cells from the blood sample; culturing the T cells in in vitro or ex vivo cell culture (where they may be contacted with the antibody, antigen binding fragment, CAR, cell or polypeptide), collecting an expanded population of T cells; mixing the T cells with an adjuvant, diluent, or carrier; administering the expanded T cells to a subject.

Accordingly, in some aspects of the present invention a method of treatment of a subject having a T-cell dysfunctional disorder is provided, the method comprising obtaining a blood sample from a subject in need of treatment, culturing T cells obtained from the blood sample in the presence of an antibody, antigen binding fragment, CAR, cell or polypeptide according to the present invention so as to expand the T cell population, collecting expanded T cells, and administering the expanded T cells to a subject in need of treatment.

The T cells may be obtained from a subject requiring treatment, and may be isolated and/or purified. They may be a $CD4^+$ and/or $CD8^+$ T-cell population. The T-cells may represent a population experiencing T cell exhaustion and may optionally have upregulated expression of CTLA-4.

During culture, T cells may be contacted with the antibody, antigen binding fragment, CAR, cell or polypeptide under conditions and for a period of time suitable to allow expansion of the T cells to a desired number of cells. After a suitable period of time the T cells may be harvested, optionally concentrated, and may be mixed with a suitable carrier, adjuvant or diluent and returned to the subject's body. A subject may undergo one or more rounds of such therapy.

Methods of T cell expansion are well known in the art, such as those described in Kalamasz et al., *J Immunother* 2004 September-October; 27(5):405-18; Montes et al., *Clin Exp Immunol* 2005 November; 142(2):292-302; Wölfl and Greenburg Nature Protocols 9 p 950-966 27 Mar. 2014; Trickett and Kwan Journal of Immunological Methods Vol. 275, Issues 1-2, 1 Apr. 2003, p 251-255; Butler et al *PLoSONE* 7(1) 12 Jan. 2012.

For example, methods of T cell expansion may comprise stimulating T cells. Stimulation may comprise non-specific stimulation, e.g. by treatment with anti-CD3/anti-CD28. Stimulation of T cells may comprise specific stimulation, e.g. by treatment with antigen (e.g. in complex with MHC, e.g. expressed by antigen presenting cells). Methods of T cell expansion may comprise culture in the presence of one or more factors for promoting T cell proliferation/expansion. For example, methods of T cell expansion may comprise culture in the presence of IL-2.

In the present invention, adoptive cell transfer (ACT) may be performed with the aim of introducing a cell or population of cells into a subject, and/or increasing the frequency of a cell or population of cells in a subject.

Adoptive transfer of T cells is described, for example, in Kalos and June 2013, Immunity 39(1): 49-60, which is hereby incorporated by reference in its entirety. Adoptive transfer of NK cells is described, for example, in Davis et al. 2015, Cancer J. 21(6): 486-491, which is hereby incorporated by reference in its entirety.

The cell may e.g. be a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. In some embodiments, the cell is a T cell. In some embodiments, the T cell is a CD3+ T cell. In some embodiments, the T cell is a CD3+, CD8+ T cell. In some embodiments, the T cell is a cytotoxic T cell (e.g. a cytotoxic T lymphocyte (CTL)). In some embodiments, the T cell is a virus-specific T cell. In some embodiments, the T cell is specific for EBV, HPV, HBV, HCV or HIV.

The present invention provides a method of treating or presenting a disease or condition in a subject, the method comprising modifying at least one cell obtained from a subject to express or comprise an antibody, antigen binding fragment, CAR, nucleic acid or vector according to the present invention, optionally expanding the modified at least one cell, and administering the modified at least one cell to a subject.

In some embodiments, the method comprises:
(a) isolating at least one cell from a subject;
(b) modifying the at least one cell to express or comprise an antibody, antigen binding fragment, CAR, nucleic acid or vector according to the present invention,
(c) optionally expanding the modified at least one cell, and;

(d) administering the modified at least one cell to a subject.

In some embodiments, the subject from which the cell is isolated is the subject administered with the modified cell (i.e., adoptive transfer is of autologous cells). In some embodiments, the subject from which the cell is isolated is a different subject to the subject to which the modified cell is administered (i.e., adoptive transfer is of allogenic cells).

The at least one cell modified according to the present invention can be modified according to methods well known to the skilled person. The modification may comprise nucleic acid transfer for permanent or transient expression of the transferred nucleic acid.

In some embodiments, the cell may additionally be modified to comprise or express a chimeric antigen receptor (CAR), or nucleic acid or vector encoding a CAR.

Any suitable genetic engineering platform may be used to modify a cell according to the present invention. Suitable methods for modifying a cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, incorporated by reference hereinabove.

In some embodiments the method may comprise one or more of the following steps: taking a blood sample from a subject; isolating and/or expanding at least one cell from the blood sample; culturing the at least one cell in in vitro or ex vivo cell culture; introducing into the at least one cell an antibody, antigen binding fragment, CAR, nucleic acid, or vector according to the present invention, thereby modifying the at least one cell; expanding the at least one modified cell; collecting the at least one modified cell; mixing the modified cell with an adjuvant, diluent, or carrier; administering the modified cell to a subject.

In some embodiments, the methods may additionally comprise treating the cell to induce/enhance expression of the antibody, antigen binding fragment, CAR, nucleic acid, or vector. For example, the nucleic acid/vector may comprise a control element for inducible upregulation of expression of the antibody, antigen binding fragment or CAR from the nucleic acid/vector in response to treatment with a particular agent. In some embodiments, treatment may be in vivo by administration of the agent to a subject having been administered with a modified cell according to the invention. In some embodiments, treatment may be ex vivo or in vitro by administration of the agent to cells in culture ex vivo or in vitro.

The skilled person is able to determine appropriate reagents and procedures for adoptive transfer of cells according to the present invention, for example by reference to Dai et al., 2016 J Nat Cancer Inst 108(7): djv439, which is incorporated by reference in its entirety.

In a related aspect, the present invention provides a method of preparing a modified cell, the method comprising introducing into a cell a an antibody, antigen binding fragment, CAR, nucleic acid or vector according to the present invention, thereby modifying the at least one cell. The method is preferably performed in vitro or ex vivo.

In one aspect, the present invention provides a method of treating or preventing a disease or condition in a subject, comprising:
(a) isolating at least one cell from a subject;
(b) introducing into the at least one cell the nucleic acid or vector according to the present invention, thereby modifying the at least one cell; and (c) administering the modified at least one cell to a subject.

In some embodiments, the cell may additionally be modified to introduce a nucleic acid or vector encoding a chimeric antigen receptor (CAR).

In some embodiments, the method additionally comprises therapeutic or prophylactic intervention, e.g. for the treatment or prevention of a cancer. In some embodiments, the therapeutic or prophylactic intervention is selected from chemotherapy, immunotherapy, radiotherapy, surgery, vaccination and/or hormone therapy.

Simultaneous or Sequential Administration

Compositions may be administered alone or in combination with other treatments, either simultaneously or sequentially dependent upon the condition to be treated.

In this specification an antibody, antigen binding fragment, CAR, cell or polypeptide of the present invention and an anti-infective agent or chemotherapeutic agent (therapeutic agent) may be administered simultaneously or sequentially.

In some embodiments, treatment with an antibody, antigen binding fragment, CAR, cell or polypeptide of the present invention may be accompanied by chemotherapy.

Simultaneous administration refers to administration of the antibody, antigen binding fragment, CAR, cell or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment, CAR, cell or polypeptide or therapeutic agent followed after a given time interval by separate administration of the other agent. It is not required that the two agents are administered by the same route, although this is the case in some embodiments. The time interval may be any time interval.

Combined inhibition of the PD-1/PD-L1 pathway and CTLA-4 blockade has been shown to provide anti-tumour efficacy—see Wolchok et al., NEJM (2013); 369:122-133. Accordingly, in one aspect the present invention provides the antibody, antigen binding fragment, CAR, cell or polypeptide according to the present invention for use in a combination therapy with an inhibitor of the PD-1/PD-L1 pathway.

In some embodiments, the present invention provides combination therapy with an inhibitor of PD-1, PD-L1 or the PD-1/PD-L1 pathway. In some embodiments, the inhibitor is an agent capable of inhibiting or preventing signalling mediated by interaction between PD-1 and PD-L1. In some embodiments, the inhibitor is an agent capable of downregulating gene or protein expression of PD-1 and/or PD-L1. In some embodiments, the inhibitor is an agent capable of inhibiting or preventing binding between PD-1 and PD-L1. In some embodiments, the agent is an antibody. In some embodiments, the agent is an antibody capable of binding to PD-1. In some embodiments, the agent is an antibody capable of binding to PD-L1. The antibody may be an antagonist antibody, or a blocking antibody. Inhibitors of PD-1, PD-L1 or the PD-1/PD-L1 pathway are well known to the skilled person, and include, for example, nivolumab, pidilizumab, BMS 936559, MPDL328oA, pembrolizumab, and avelumab. PD-1/PDL-1 inhibitors contemplated for use in accordance with the present invention include those described in Sunshine and Taube "PD-1/PD-L1 inhibitors", Curr. Opin. Pharmacol. 2015, 23:32-38, which is hereby incorporated by reference in its entirety.

Anti-Infective Agents

In treating infection, an antibody, antigen binding fragment, CAR, cell or polypeptide of the present invention may be administered in combination with an anti-infective agent, as described above. The anti-infective agent may be an agent known to have action against the microorganism or virus responsible for the infection.

Suitable anti-infective agents include antibiotics (such as penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins), anti-viral agents (such as reverse transcriptase inhibitors, integrase inhibitors, transcription factor inhibitors, antisense and siRNA agents and protease inhibitors), anti-fungal agents (such as polyenes, imidazoles, triazoles, thiazoles, allylamines, and echinocandins) and anti-parasitic agents (such as antinematode agents, anticestode agents, antitrematode agents, antiamoebic agents and antiprotozoal agents).

Chemotherapy

Chemotherapy refers to treatment of a cancer with a drug or with ionising radiation (e.g. radiotherapy using X-rays or γ-rays). In preferred embodiments chemotherapy refers to treatment with a drug. The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc.

For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracycline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inhibitors such as erlotinib, cetuximab and gefitinib; anti-angiogenic agents such as bevacizumab (Avastin®); cancer vaccines such as Sipuleucel-T (Provenge®).

In one embodiment the chemotherapeutic agent is an anti-PD-1 antibody, anti-PD-L1 antibody, anti-TIM-3 antibody, anti-LAG-3, anti-41 BB, anti-GITR, anti-CD27, anti-BLTA, anti-OX43, anti-VEGF, anti-TNFα, anti-IL2, anti-GpIIb/IIIa, anti-CD-52, anti-CD20, anti-RSV, anti-HER2/neu(erbB2), anti-TNF receptor, anti-EGFR or other antibody. In some embodiments, the chemotherapeutic agent is an immune checkpoint inhibitor or costimulation molecule.

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar™, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron™, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Routes of Administration

Antibodies, antigen binding fragments, CARs, cells, polypeptides and other therapeutic agents, medicaments and pharmaceutical compositions according to aspects of the present invention may be formulated for administration by a number of routes, including but not limited to, parenteral, intravenous, intra-arterial, intramuscular, subcutaneous, intradermal, intratumoral and oral. Antibodies, antigen binding fragments, CARs, cells, polypeptides and other therapeutic agents, may be formulated in fluid or solid form. Fluid formulations may be formulated for administration by injection to a selected region of the human or animal body.

Dosage Regime

Multiple doses of the antibody, antigen binding fragment, CAR, cell or polypeptide may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment, CAR, cell or polypeptide. The kit may provide the antibody, antigen binding fragment, CAR, cell or polypeptide in the form of a medicament or pharmaceutical composition, and may be provided together with instructions for administration to a patient in order to treat a specified disease or condition. The antibody, antigen binding fragment, CAR, cell or polypeptide may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Protein Expression

Molecular biology techniques suitable for producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include E. coli. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

The following numbered paragraphs (paras) describe particular aspects and embodiments of the present invention:

1. A method of treating cancer, comprising administering an antibody or antigen binding fragment to a patient suffering from a cancer, wherein the antibody or antigen binding fragment binds to CTLA-4, and comprises:

at least one light chain variable region incorporating the following CDRs:

```
LC-CDR1:
                                    (SEQ ID NO: 5)
RATQGISSWLA

LC-CDR2:
                                    (SEQ ID NO: 6)
AASSLQS
```

```
LC-CDR3:
                        (SEQ ID NO: 7)
QQANTLPLFT;
``` at least one heavy chain variable region incorporating the following CDRs:

```
HC-CDR1:
                        (SEQ ID NO: 8)
SNTAAWN

HC-CDR2:
                        (SEQ ID NO: 9)
RTYYRSKWYSDYGLSVKS

HC-CDR3:
                        (SEQ ID NO: 10)
EGSGGTLIY.
```

2. The method of para 1, wherein the antibody or antigen binding fragment comprises a heavy chain variable region sequence having at least 85% sequence identity to the amino acid sequence of SEQ ID NO:3 or 4, and a light chain variable region sequence having at least 85% sequence identity to the amino acid sequence of SEQ ID NO:1 or 2.

3. The method of para 1, wherein the antibody or antigen binding fragment comprises a heavy chain variable region comprising the amino acid sequence of SEQ ID NO:3 or 4, and a light chain variable region comprising the amino acid sequence of SEQ ID NO:1 or 2.

4. The method of para 1, wherein the cancer is a cancer of a tissue selected from the group consisting of colon, rectum, nasopharynx, cervix, oropharynx, stomach, liver, head and neck, oral cavity, oesophagus, lip, mouth, tongue, tonsil, nose, throat, salivary gland, sinus, pharynx, larynx, prostate, lung, bladder, skin, kidney, ovary or mesothelium, or wherein the cancer is selected from the group consisting of colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer and mesothelioma.

5. The method of para 1, wherein the administration of the antibody or antigen binding fragment is intravenous.

6. The method of para 1, wherein the antibody comprises a human constant region selected from IgG1, IgG2, IgG3 and IgG4.

7. The method of para 1, wherein the antigen binding fragment is a Fab fragment or scFv fragment.

8. The method of para 1, wherein the antigen binding fragment is comprised in a chimeric antigen receptor (CAR).

9. A method of treating cancer, comprising administering an antibody or antigen binding fragment to a patient suffering from a cancer, wherein the antibody or antigen binding fragment binds to CTLA-4, and comprises:
a heavy chain variable region comprising the amino acid sequence of SEQ ID NO:3 or 4,
and
the light chain variable region comprising the amino acid sequence of SEQ ID NO:1 or 2.

10. The method of para 9, wherein the cancer is a cancer of a tissue selected from the group consisting of colon, rectum, nasopharynx, cervix, oropharynx, stomach, liver, head and neck, oral cavity, oesophagus, lip, mouth, tongue, tonsil, nose, throat, salivary gland, sinus, pharynx, larynx, prostate, lung, bladder, skin, kidney, ovary or mesothelium, or wherein the cancer is selected from the group consisting of colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer and mesothelioma.

11. The method of para 9, wherein the administration of the antibody or antigen binding fragment is intravenous.

12. The method of para 9, wherein the antibody comprises a human constant region selected from IgG1, IgG2, IgG3 and IgG4.

13. The method of para 9, wherein the antigen binding fragment is a Fab fragment or scFv fragment.

14. The method of para 9, wherein the antigen binding fragment is comprised in a chimeric antigen receptor (CAR).

15. A method of treating cancer in a subject, comprising:
culturing T cells obtained from a blood sample from a subject having a cancer in the presence of an antibody or antigen binding fragment which binds to CTLA-4 to expand a T cell population; and
administering the expanded T cell population to the subject;
wherein the antibody or antigen binding fragment which binds to CTLA-4 comprises: at least one light chain variable region incorporating the following CDRs:

```
LC-CDR1:
                        (SEQ ID NO: 5)
RATQGISSWLA

LC-CDR2:
                        (SEQ ID NO: 6)
AASSLQS

LC-CDR3:
                        (SEQ ID NO: 7)
QQANTLPLFT;
``` at least one heavy chain variable region incorporating the following CDRs:

```
HC-CDR1:
                        (SEQ ID NO: 8)
SNTAAWN

HC-CDR2:
                        (SEQ ID NO: 9)
RTYYRSKWYSDYGLSVKS

HC-CDR3:
                        (SEQ ID NO: 10)
EGSGGTLIY.
```

16. The method of para 15, wherein the antibody or antigen binding fragment comprises a heavy chain variable region comprising the amino acid sequence of SEQ ID NO:3 or 4, and a light chain variable region comprising the amino acid sequence of SEQ ID NO:1 or 2.

17. The method of para 15 wherein the cancer is a cancer of a tissue selected from the group consisting of colon, rectum, nasopharynx, cervix, oropharynx, stomach, liver, head and neck, oral cavity, oesophagus, lip, mouth, tongue, tonsil, nose, throat, salivary gland, sinus, pharynx, larynx, prostate, lung, bladder, skin, kidney, ovary or mesothelium, or wherein the cancer is selected from the group consisting of colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer and mesothelioma.

18. The method of para 15, wherein the antibody comprises a human constant region selected from IgG1, IgG2, IgG3 and IgG4.

19. The method of para 15, wherein the antigen binding fragment is a Fab fragment or scFv fragment.

20. The method of para 15, wherein the antigen binding fragment is comprised in a chimeric antigen receptor (CAR).

BRIEF DESCRIPTION OF THE FIGURES

Embodiments and experiments illustrating the principles of the invention will now be discussed with reference to the accompanying figures in which:

FIG. 1. Light chain variable domain sequences for anti-CTLA-4 antibody clones 2C8 and 2C8_gl. CDRs are underlined and shown separately.

FIG. 2. Heavy chain variable domain sequences for anti-CTLA-4 antibody clones 2C8 and 2C8_gl. CDRs are underlined and shown separately.

FIG. 3. Nucleotide and encoded amino acid sequences of heavy and light chain variable domain sequences for anti-CTLA-4 antibody clones 2C8 and 2C8_gl.

EXAMPLES

The inventors describe in the following Examples isolation and characterisation of an anti-CTLA-4 antibody, which is shown to bind to human and mouse CTLA-4, not to bind to human CD28, to be capable of blocking interaction of CTLA-4 and CD80, to inhibit CTLA-4/CD80 and CTLA-4/CD86 signalling, and to display anti-cancer activity in vivo.

Example 1: Isolation of Anti-Human CTLA-4 Antibody Clone 2C8

Figure 4:
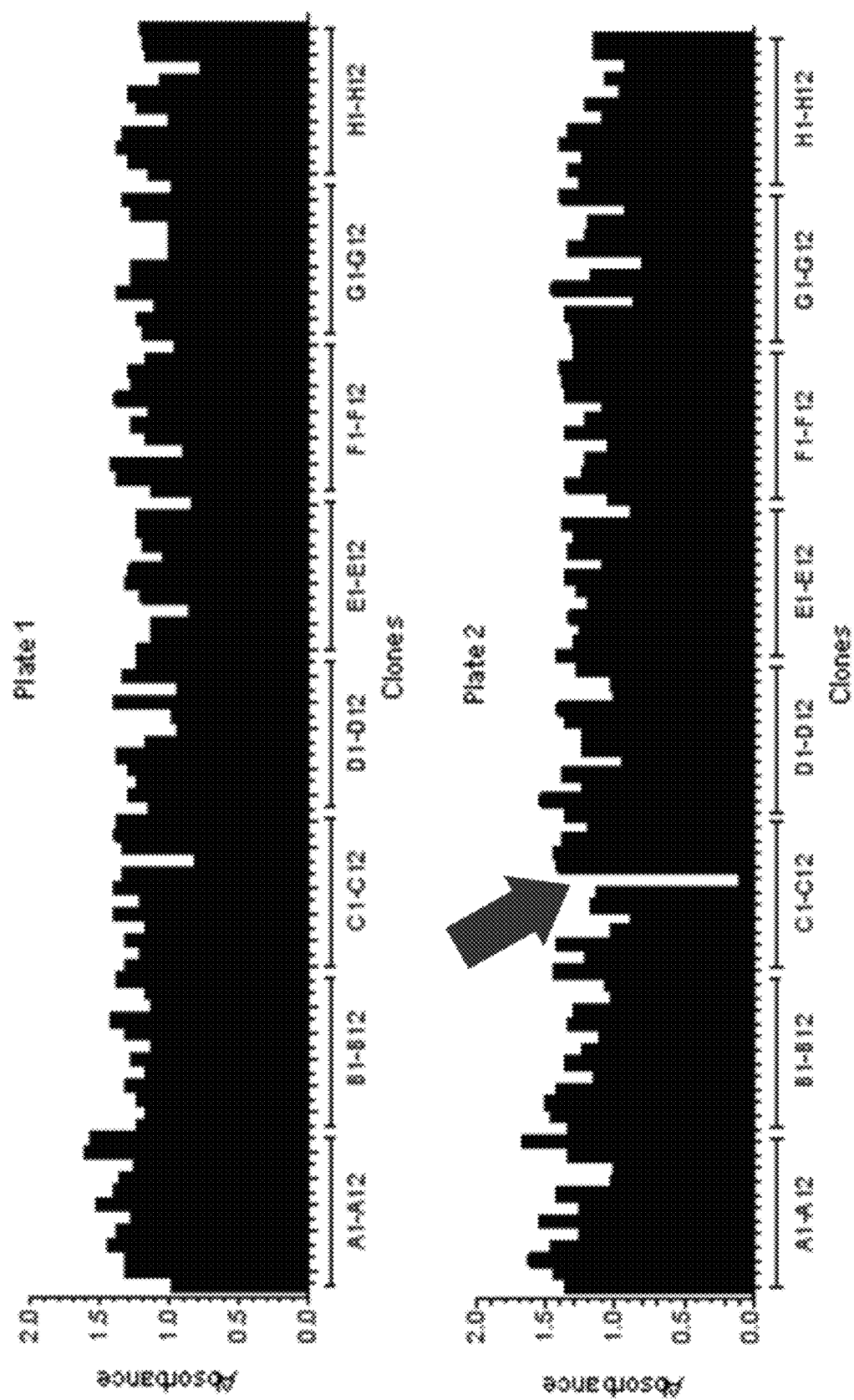
FIG. 4. Bar charts showing selection of anti-human CTLA-4 hits after biopanning. Fabs were mixed with human CTLA-4, and binding to CD80 was analysed by ELISA. Arrow indicates clone 2C8, which was identified as being an efficient blocker of CTLA-4 binding to CD80.
Figure 4:
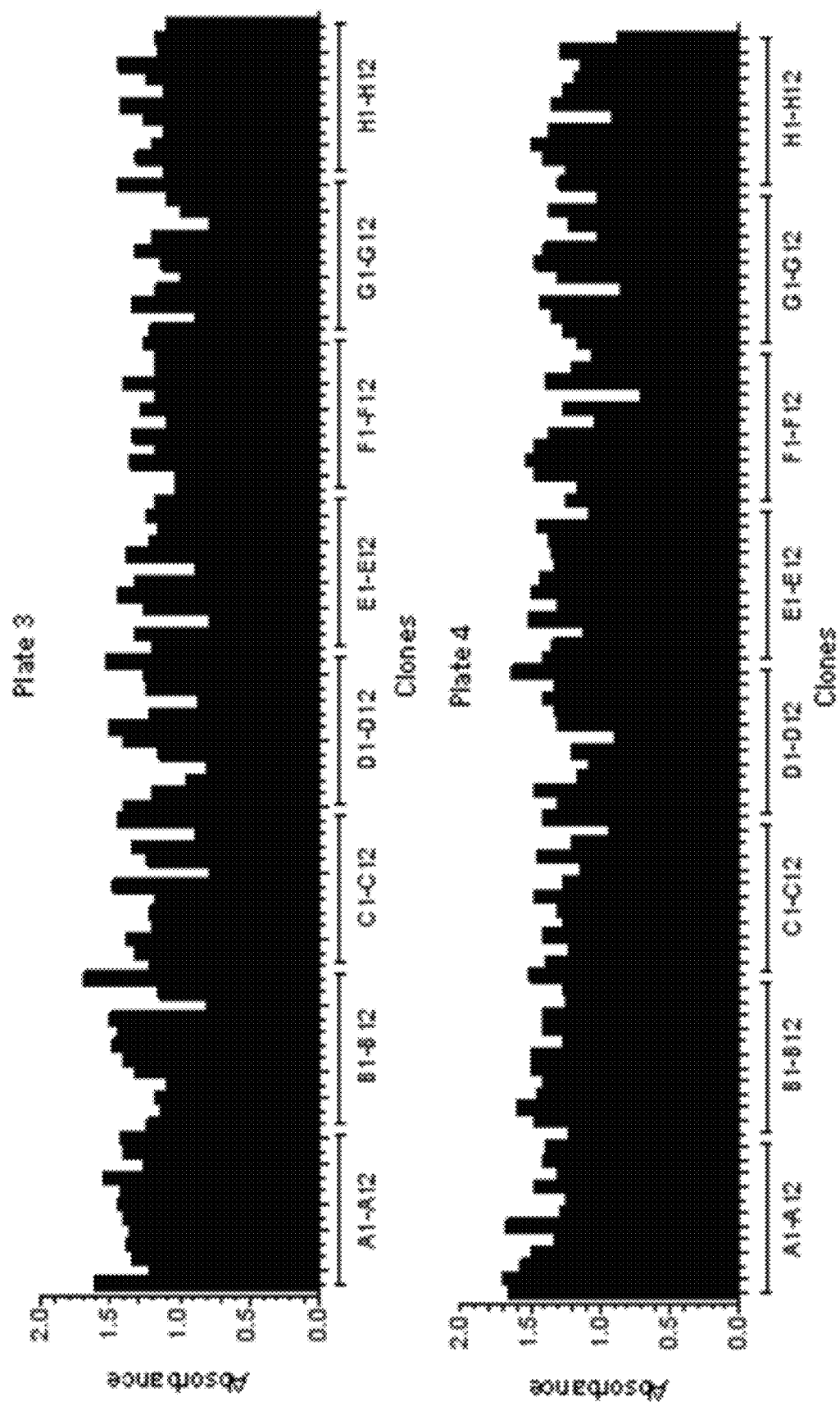

Anti-CTLA-4 antibodies were isolated from a human antibody phage display library via in vitro selection. Antibodies were screened for ability to block the binding of CTLA-4 to its ligand in a blocking ELISA. Out of 384 clones tested, clone 2C8 was the only clone to show a drastic inhibition of CTLA-4 binding (FIG. 4).

Example 2: Analysis of Binding of 2C8 to Human CTLA-4

Figure 5:
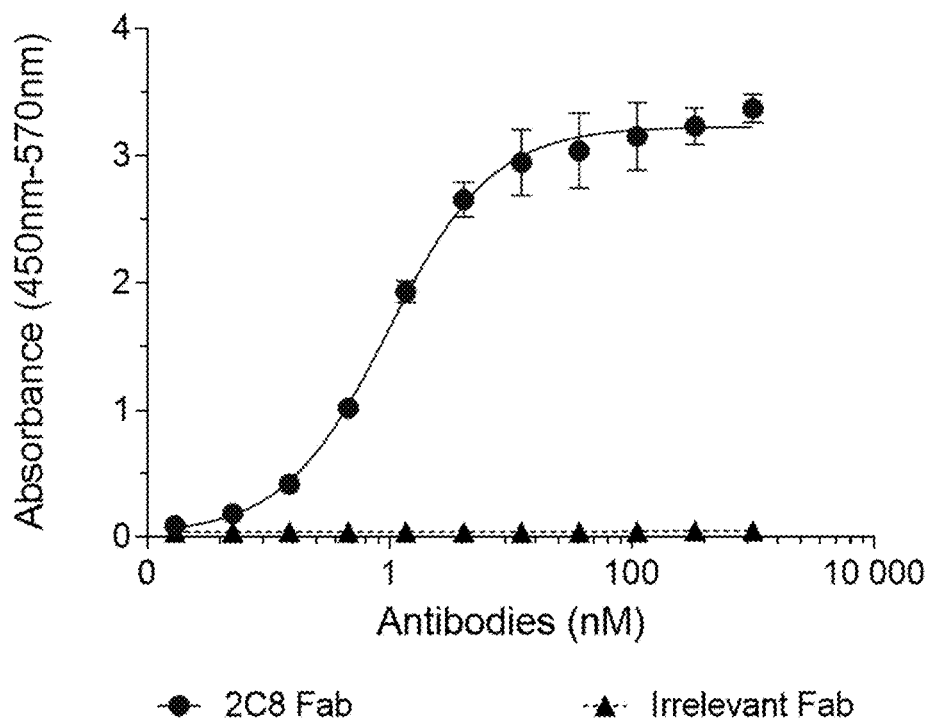
FIG. 5. Graph showing results of ELISA analysis of binding of 2C8 Fab to human CTLA-4.
Figure 6:
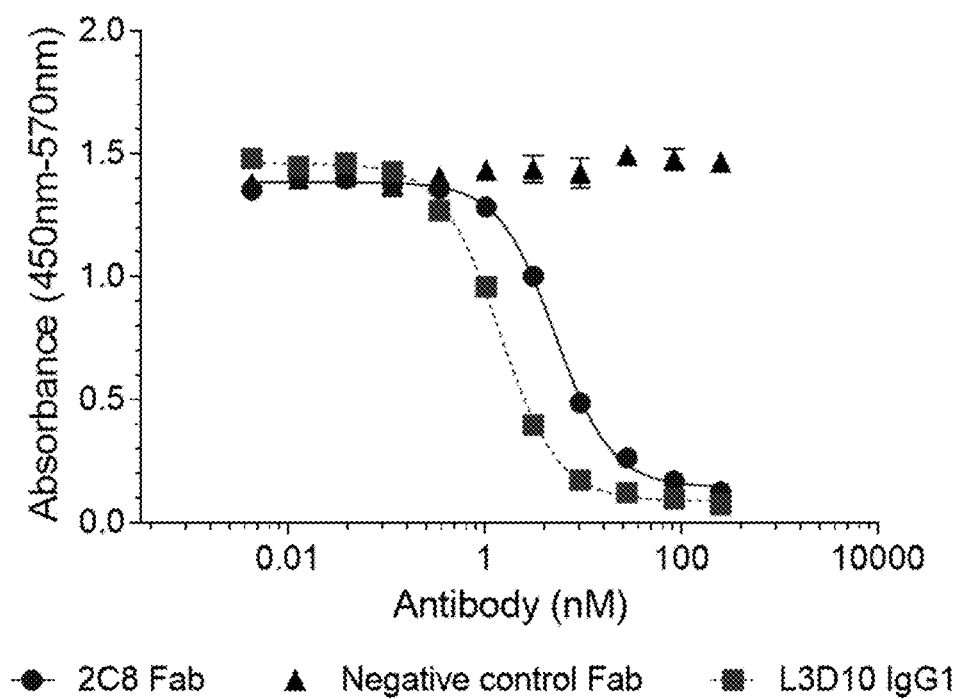
FIG. 6. Graph showing results of ELISA analysis of blocking of binding of CTLA-4 to CD80 binding by 2C8 Fab.

Binding of 2C8 to human CTLA-4 was analysed by ELISA. Human CTLA-4 was coated onto ELISA plates, and 2C8 Fab or negative control Fab was added at various concentrations. The results are shown in FIG. 5. 2C8 showed ability to bind strongly to human CTLA-4, in a dose-dependent manner.

Example 3: Analysis of Blocking of Interaction Between Human CTLA-4 and CD80

The ability of 2C8 to inhibit binding of CTLA-4 to its ligand, CD80, was analysed by ELISA. Briefly, CD80 was coated onto ELISA plates. 2C8, a negative control Fab or L3D10 (a commercial mouse anti-human CTLA-4 IgG1) were pre-incubated with human CTLA-4, and then before being added onto the ELISA plates. Binding of CTLA-4 to CD80 was determined by ELISA.

The results are shown in FIG. 3. 2C8 was shown to block interaction between CTLA-4 and CD80.

Example 4: Engineering 2C8 to 2C8_gl

Antibody clone 2C8 was expressed as a human IgG1. Framework regions of 2C8 variable domains were engineered to revert to a germline-like immunoglobulin, and the engineered clone was named 2C8_gl.

Example 5: Analysis of Species Cross-Reactivity

Ability of 2C8 to recognise mouse CTLA-4 was analysed by ELISA. 2C8 IgG, 2C8_gl IgG and a commercial rat anti-mouse CTLA-4 IgG were coated into ELISA plates. Mouse CTLA-4 was biotinylated, and then added to the ELISA plates at various concentrations. The binding of mouse CTLA-4 to the antibodies was revealed using streptavidin-HRP.

Figure 7:
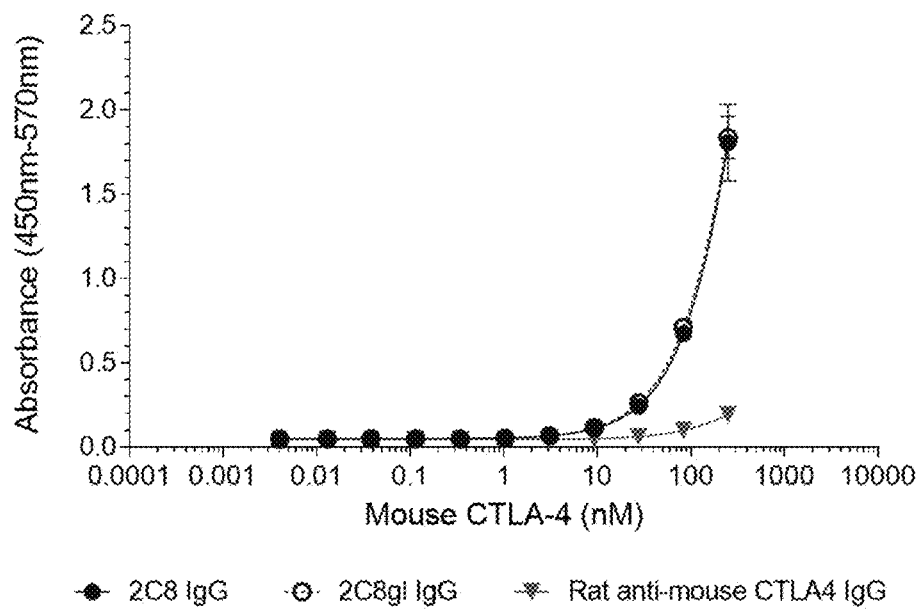
FIG. 7. Graph showing results of ELISA analysis of binding of 2C8 IgG to mouse CTLA-4.

The results are shown in FIG. 7. 2C8 was shown to be capable of recognising mouse CTLA-4, and with much greater efficiency than the commercial positive control. The germline reversion engineering did not affect the binding capacity of the antibody as 2C8_gl which showed an identical binding profile to 2C8 (FIG. 7).

Example 6: Analysis of Cross Species Reactivity; Binding to Cynomolgus and Rhesus CTLA-4

Figure 14:
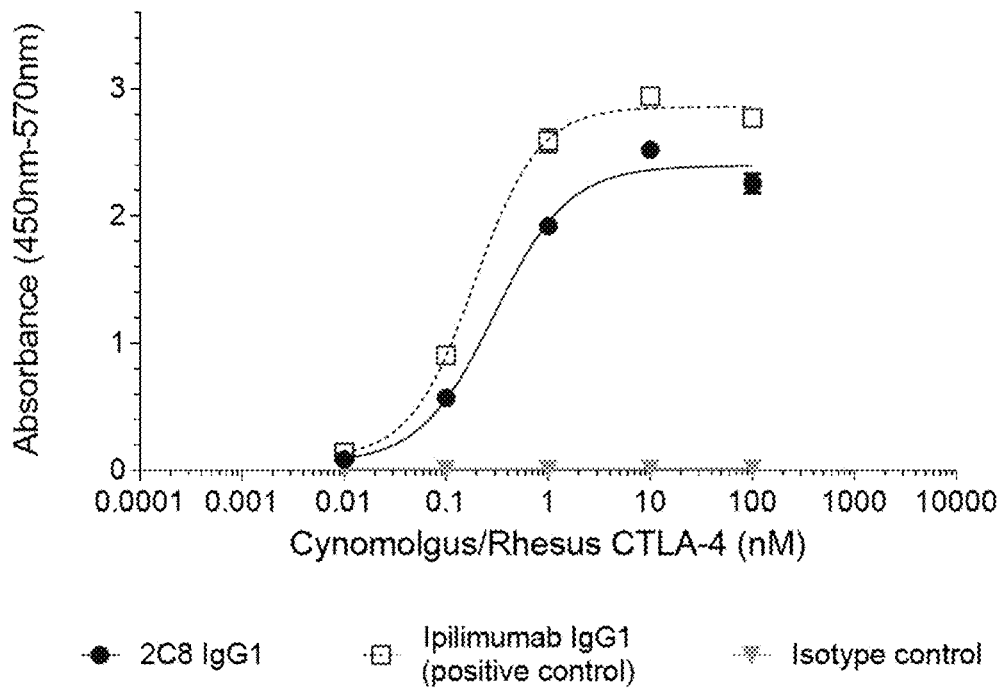
FIG. 14. Chart showing binding of 2C8 to cynomolgus/rhesus CTLA-4.

A similar ELISA was conducted with Cynomolgus/Rhesus CTLA-4. Ipilimumab was used as a positive control. 2C8 strongly recognised cynomolgus/rhesus CTLA-4 (FIG. 14).

Example 7: Analysis of Cross-Reactivity with CD28

CTLA-4 shares its ligands with CD28. Whilst CD28 transmits a stimulatory signal to T cells upon binding to CD80 and CD86, CTLA-4 sends an inhibitory signal. Binding of 2C8 to CD28 was investigated by ELISA. Human CD28 conjugated to human Fc was coated onto ELISA plates, and various concentrations of anti-CTLA-4 or negative control antibodies were added.

Figure 8:
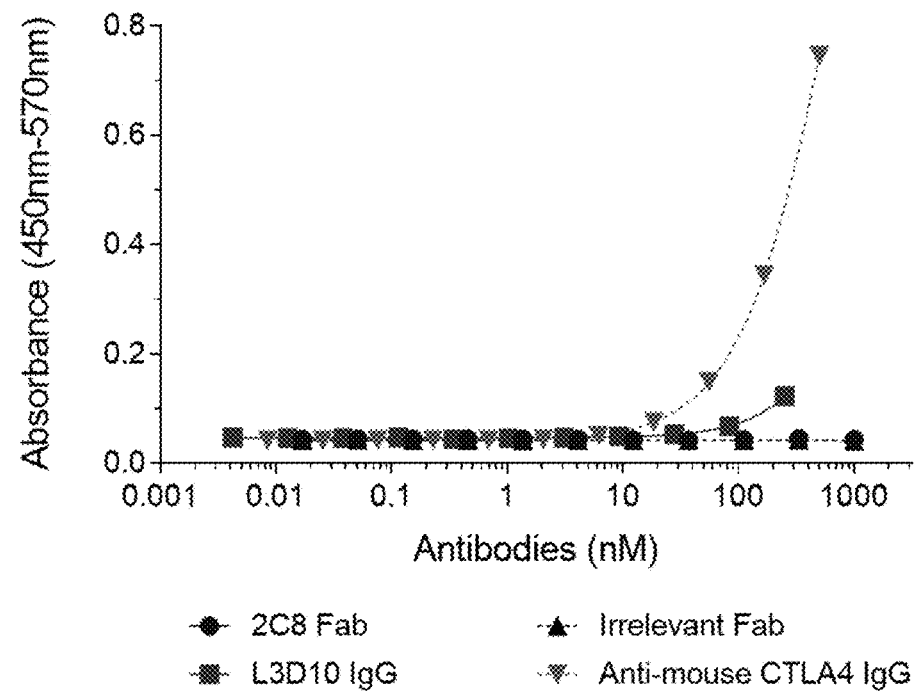
FIG. 8. Graph showing results of ELISA analysis of binding of 2C8 to human CD28.

The results are shown in FIG. 8. Unlike the commercial rat anti-mouse CTLA-4 IgG, 2C8 displayed no binding to CD28 at all, even at high concentrations of the antibody (FIG. 5). In particular, 2C8 displayed less binding of CD28 than L3D10.

Example 8: Analysis of Affinity of Binding of 2C8 to CTLA-4

Figure 9:
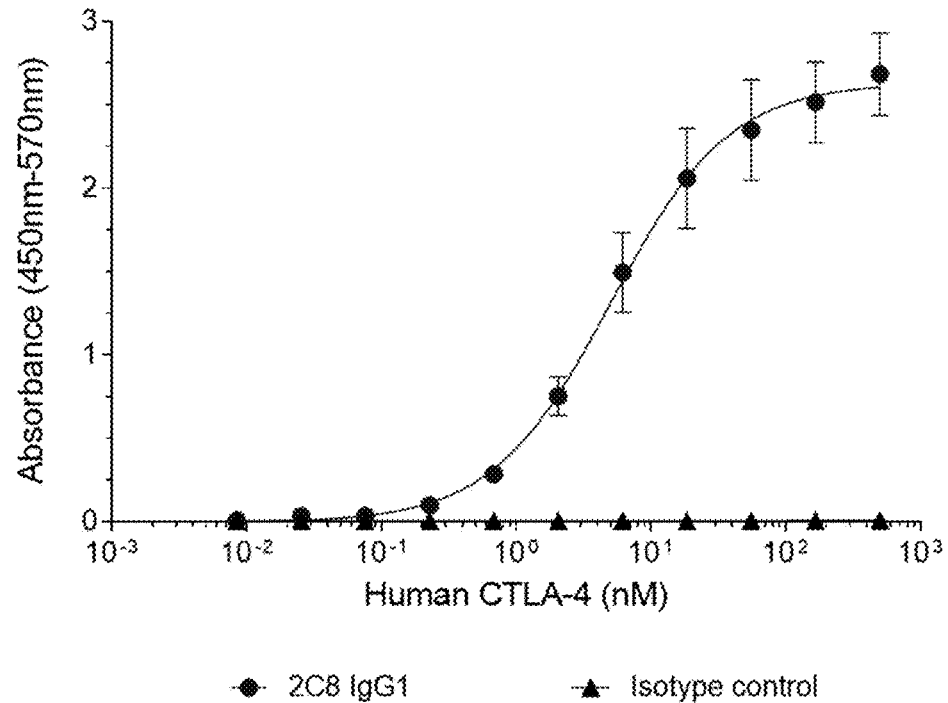
FIG. 9. Graph showing results of ELISA analysis of binding affinity of binding of 2C8 to human CTLA-4. Shown are mean Absorbance±SD on 2 independent experiments both performed in duplicates.

Binding affinity of antibody 2C8 to CTLA-4 was measured by ELISA. Antibodies were coated on the plates and human CTLA-4 was added at different concentrations. Dose response curve were plotted (see FIG. 9) and the effective concentration 50% (EC50) was calculated. In this assay, 2C8 showed a mean EC50 of 5.0 nM (from 2 independent experiments).

Figure 15:
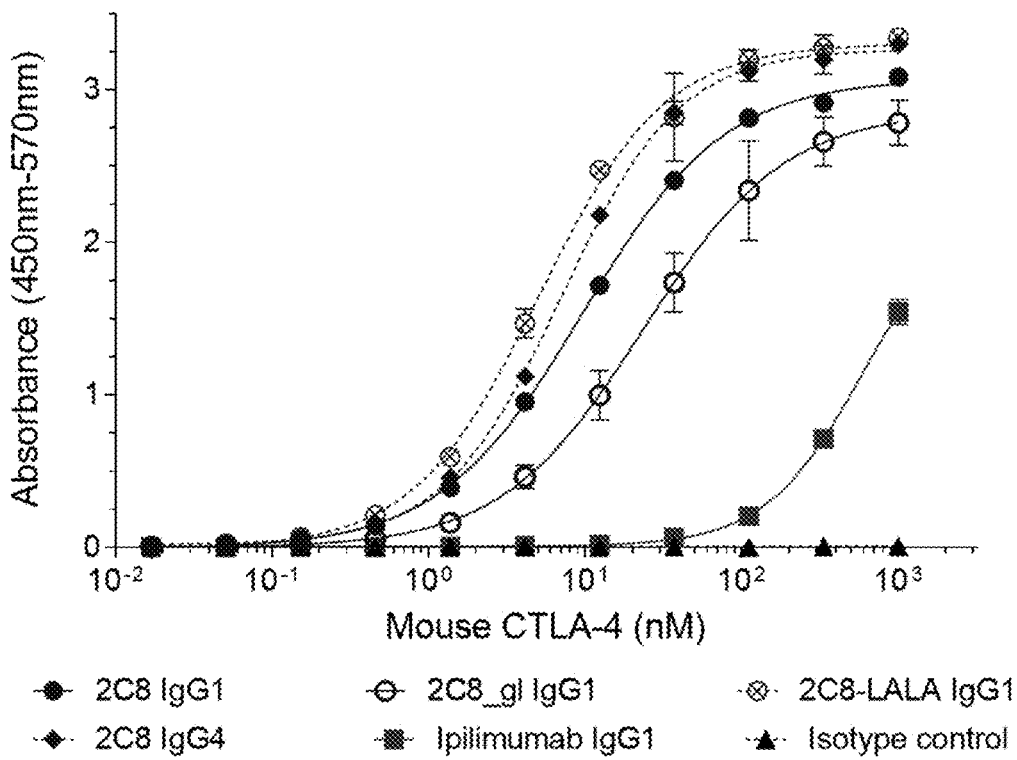
FIG. 15. Chart showing binding affinity for mouse CTLA-4. Shown are mean Absorbance±SD on duplicates with IgG1 versions of 2C8, 2C8gl and 2C8 with LALA mutation, with the IgG4 version of 2C8, with Ipilimumab (a human anti-huCTLA-4) and an IgG1 isotype control.

The binding affinity for mouse CTLA-4 was measured similarly and the EC50 for mouse CTLA-4 extrapolated; 2C8 IgG1 showed an EC50 of 9.6 nM (23.5 nM for 2C8_gl IgG1, 5.1 nM for 2C8 IgG1 with LALA mutation and 7.0 nM for 2C8 IgG4) (FIG. 15). The "LALA" mutation refers to mutation of leucine residues at positions 234 and 234 of the of the Fc region to alanine (i.e. L234A, L235A); this mutation is known to weaken interaction between Fc and Fc-γR, and therefore to prevent ADCC activity (see e.g. Hezareh et al., J Virol (2001) 75(24):12161-12168).

Affinity of binding of 2C8 to human CTLA-4 was also measured by Surface Plasmon Resonance (SPR) analysis. The antibody was immobilised onto a biosensor chip, human CTLA-4 was flowed over at different concentrations, and the response was measured. In this assay, 2C8 showed an affinity of binding ($K_D$) of 9.6 nM.

Example 9: Analysis of Avidity of Binding of 2C8 to CTLA-4

Figure 10:
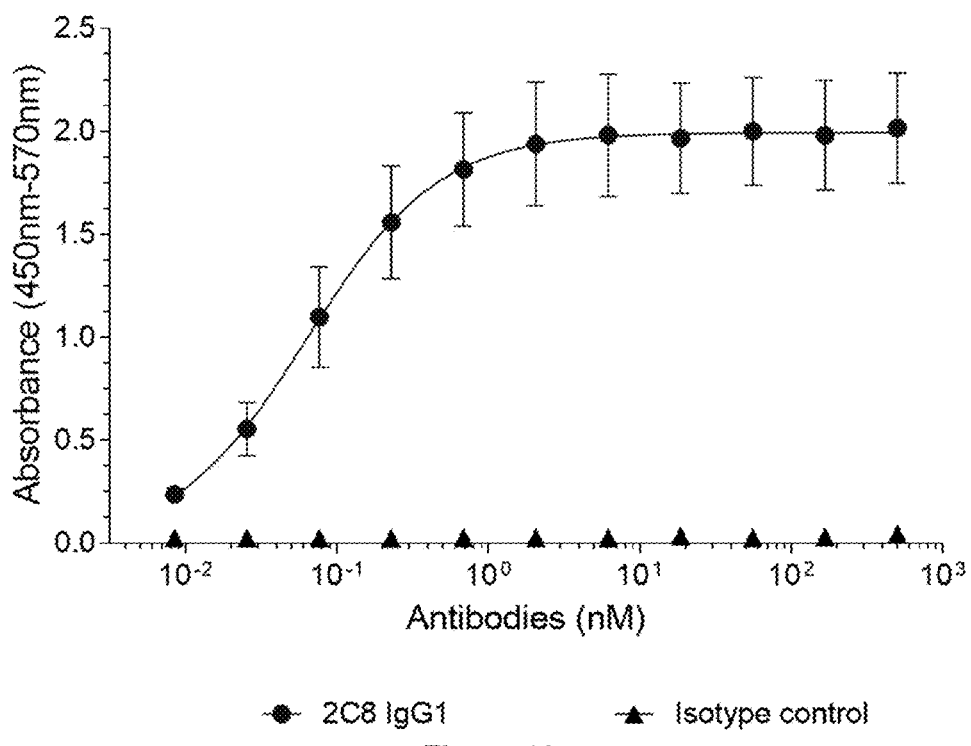
FIG. 10. Graph showing results of ELISA analysis of avidity of binding of 2C8 to human CTLA-4.

Avidity of binding of 2C8 to human CTLA-4 was analysed by ELISA. Briefly, human CTLA-4 was coated onto ELISA plates and the anti-human CTLA-4 antibody was added to the ELISA plates at various concentrations. The response curve was plotted (see FIG. 10), and EC50 was calculated. The mean EC50 for 2C8 in independent assays was 63.6 pM.

Figure 16:
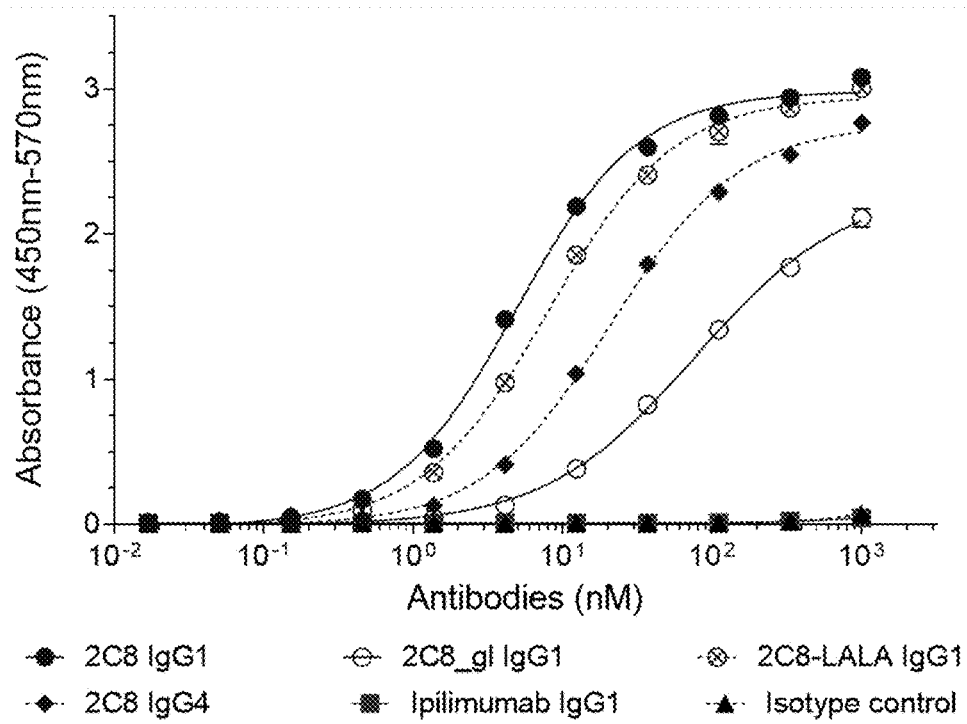
FIG. 16. Chart showing binding avidity for mouse CTLA-4. Shown are mean Absorbance±SD on duplicates with IgG1 versions of 2C8, 2C8gl and 2C8 with LALA mutation, with the IgG4 version of 2C8, with Ipilimumab (an anti-huCTLA-4 which is known for not cross-reacting with mouse CTLA-4) and an IgG1 isotype control.

The avidity for mouse CTLA-4 was measured similarly by ELISA (FIG. 16). With the mouse protein, the EC50 is of 4.9 nM for 2C8 IgG1 (77.1 nM for 2C8_gl IgG1; 8.0 nM for 2C8 IgG1 with LALA mutation; 20.9 nM for 2C8 IgG4).

Example 10: Analysis of Binding to CTLA-4 Expressed on Cell Surface

HEK-293.6E cells were transfected with human or mouse CTLA-4. Overexpressing cells were then incubated in the presence of 2C8 or an isotype control and binding of the antibodies to the cells was measured by flow cytometry.

Figure 17:
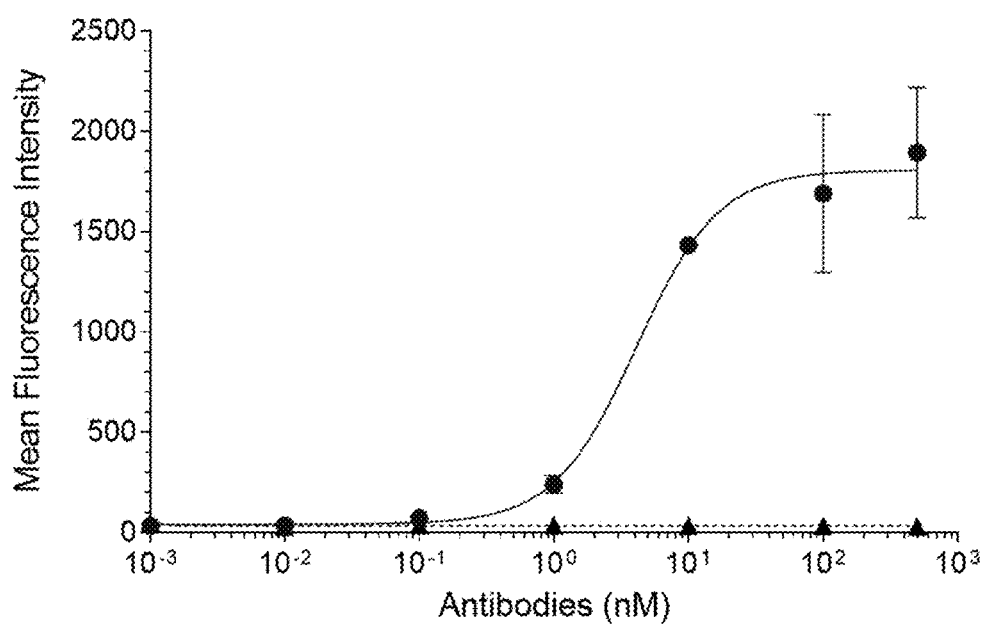
FIG. 17. Chart showing binding of 2C8 onto HEK-293.6E cells transfected with human CTLA-4. Shown are mean Mean Fluorescence Intensities±SD on duplicates.
Figure 18:
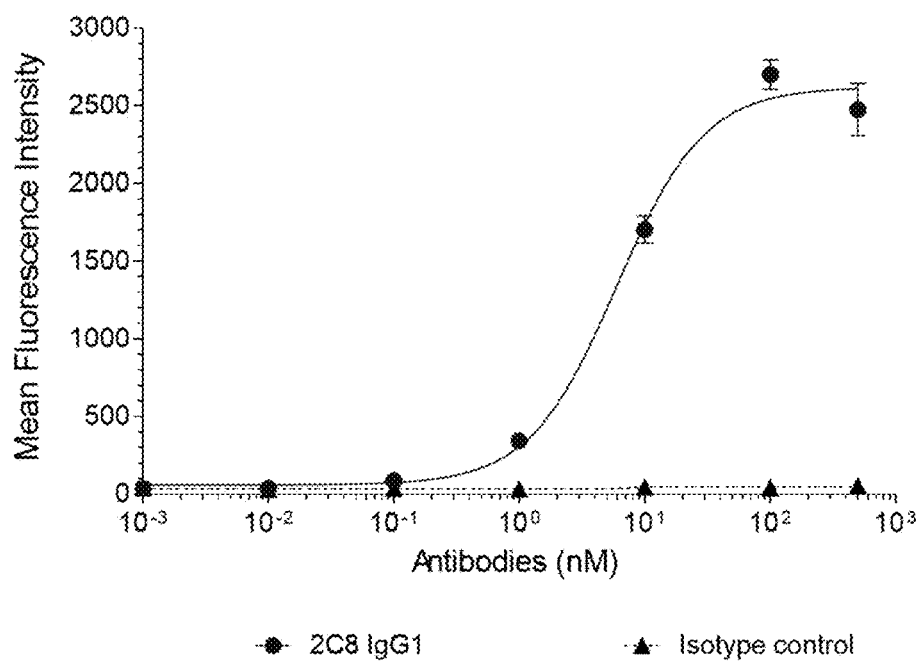
FIG. 18. Chart showing binding of 2C8 onto HEK-293.6E cells transfected with mouse CTLA-4. Shown are mean Mean Fluorescence Intensities±SD on duplicates.
Figure 19A:
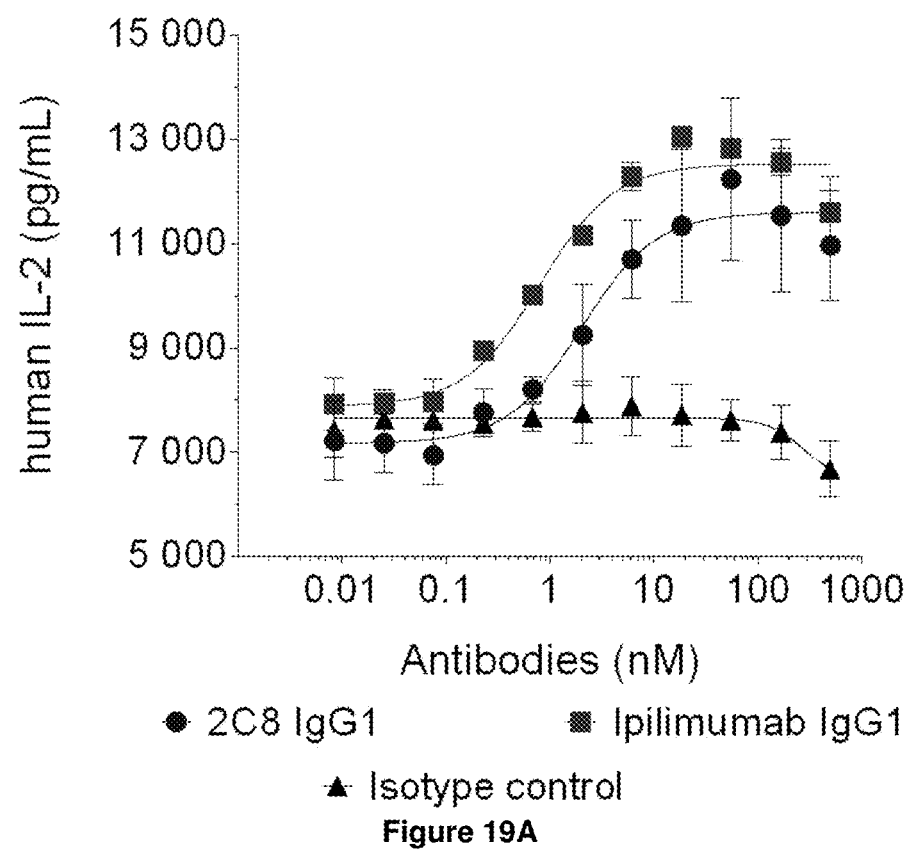
FIG. 19A to 19D. Charts showing restoration of T cells activity by 2C8 or derived antibodies after CTLA-4-induced inhibition of activation. Shown are mean±SD of secreted IL-2 on duplicates in 4 independent experiments (A to D) using Ipilimumab as a positive control and an IgG1 isotype control.
Figure 19B:
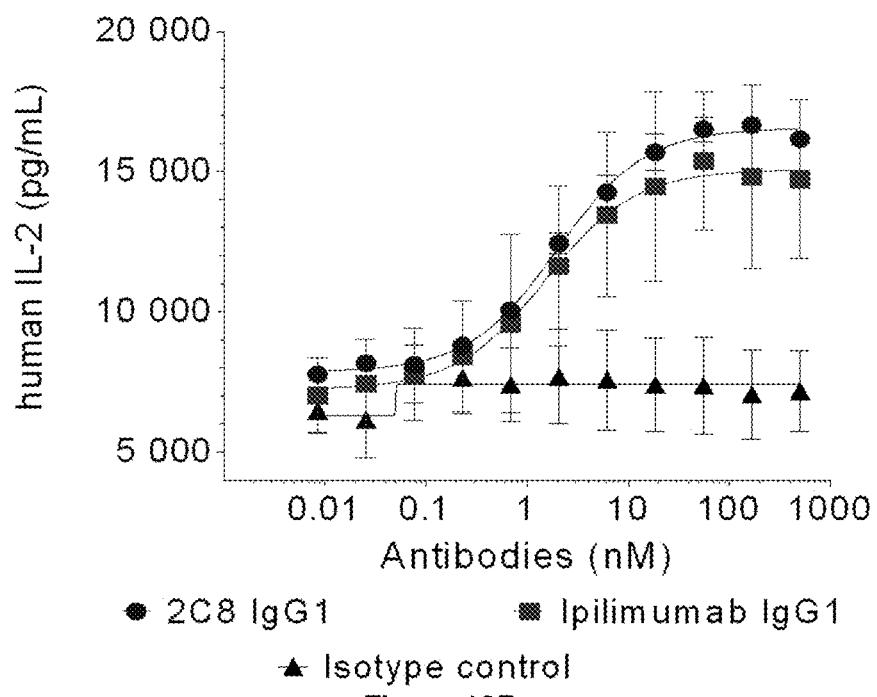
Figure 19C:
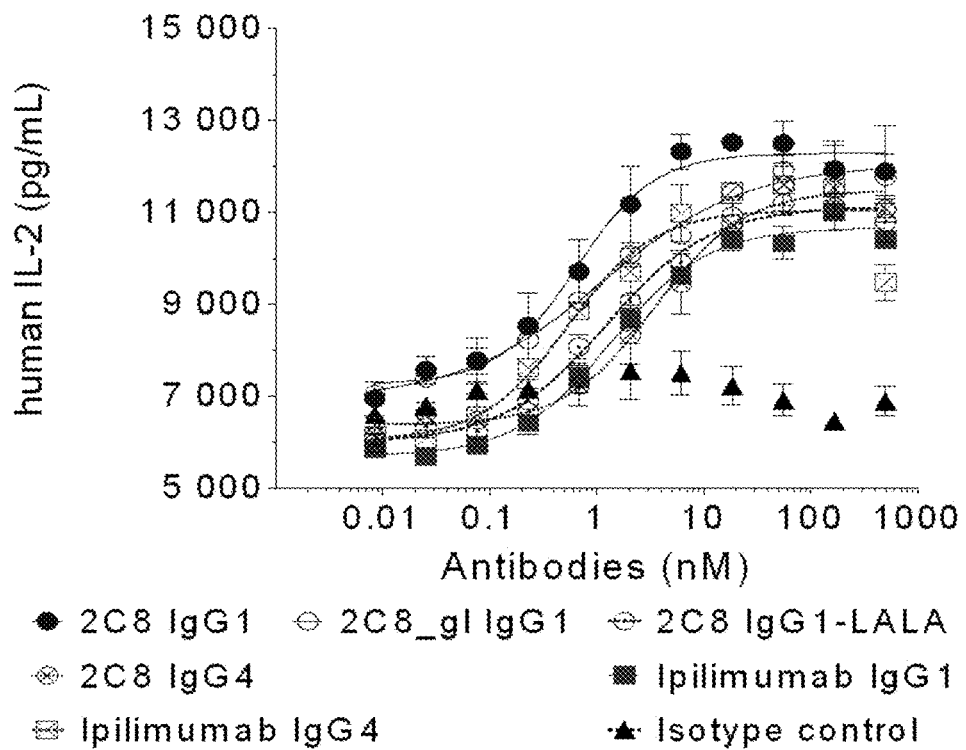
Figure 19D:
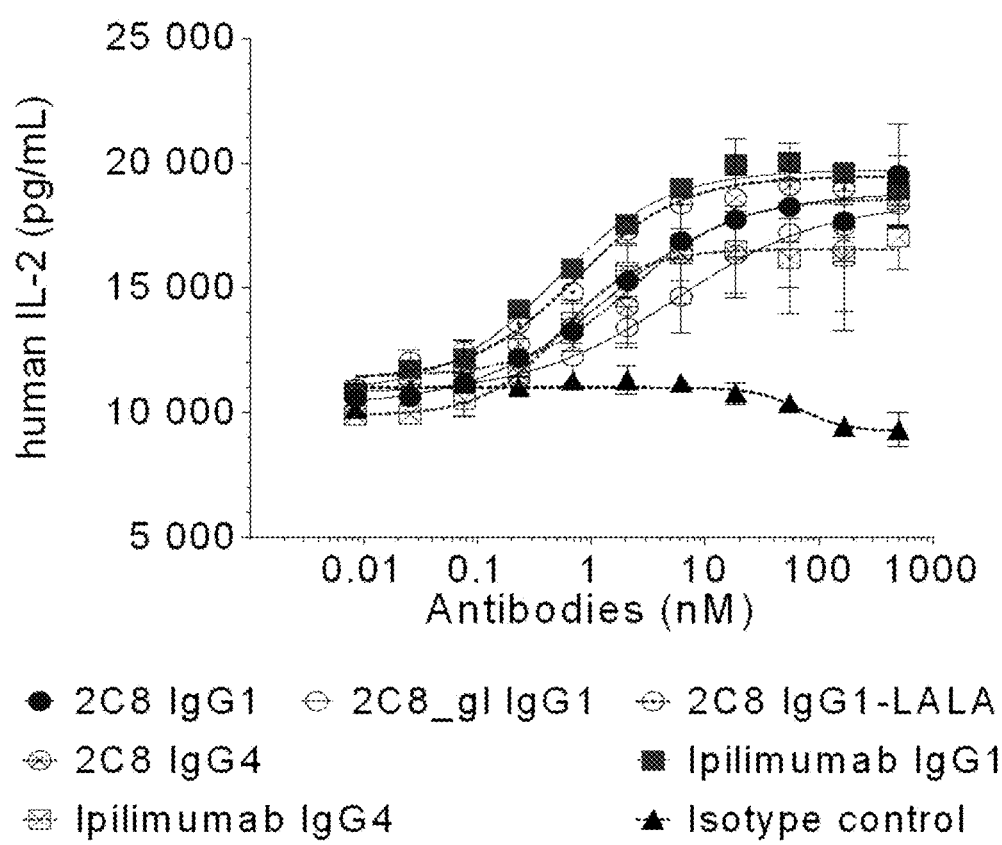

2C8 was able to efficiently bind to cell surface-expressed human CTLA-4 (FIG. 17) or mouse CTLA-4 (FIG. 18) in these assays.

Example 11: Analysis of In Vitro Activity of Anti-CTLA-4 Antibody 2C8

Figure 11:
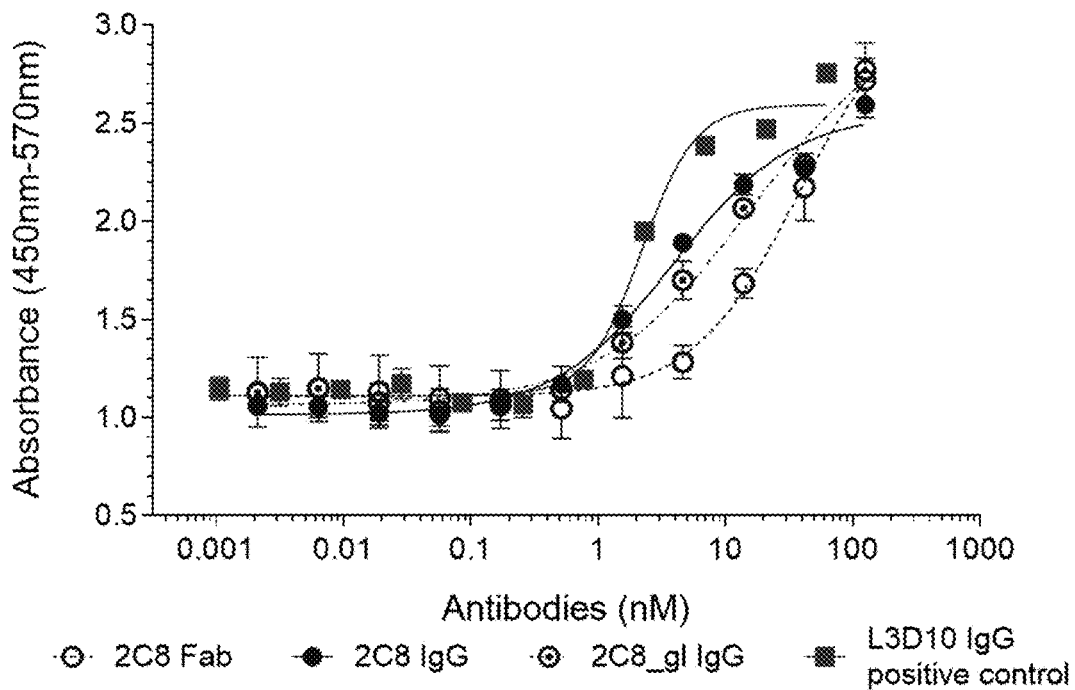
FIG. 11. Chart showing restoration of T cells activity by 2C8 after CTLA-4-induced inhibition of activation via CD80. Shown are mean±SD on duplicates in 2 independent experiments of the Absorbance measurement corresponding to IL-2 concentration in supernatants.

A T cell reactivation assay was performed to analyse activity of the antibody. In the assay, Jurkat T cells are stimulated with phytohemagglutinin and either CD80 or CD86. Following such treatment, cells secrete IL-2. Addition of CTLA-4 inhibits stimulation and secretion of IL-2. The level of cell activation, i.e. secretion of IL-2, in the presence of anti-CTLA-4 and control antibodies was measured by ELISA (FIG. 11). In reactivation assays, either ipilimumab (human anti-huCTLA-4 marketed as Yervoy®) or L3D10 (commercial mouse anti-huCTLA-4 IgG1κ) was used as a positive control.

Figure 12:
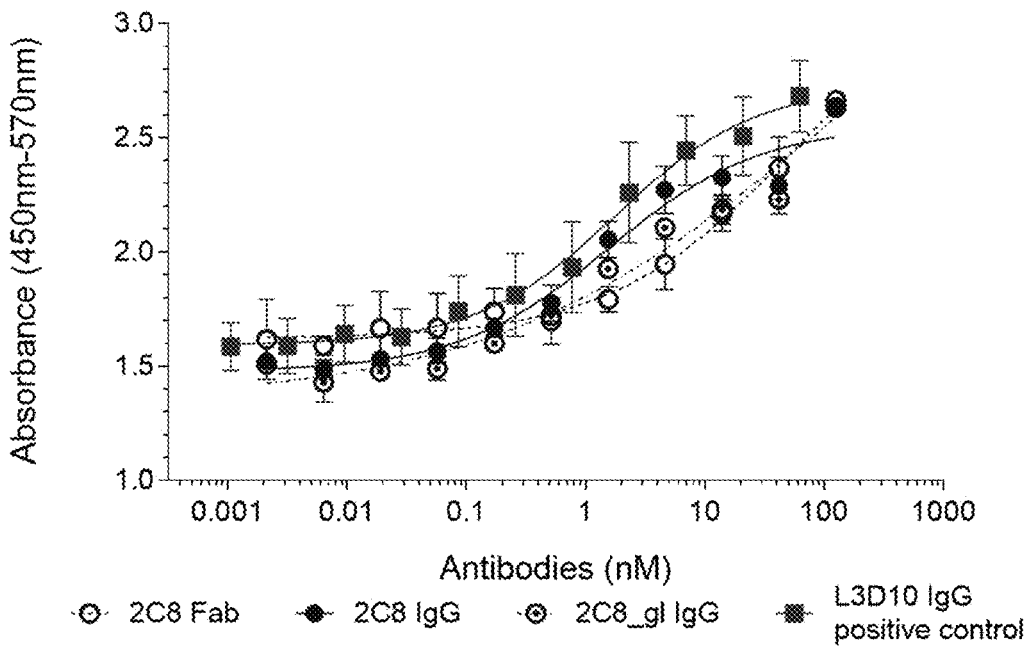
FIG. 12. Chart showing restoration of T cells activity by 2C8 after CTLA-4-induced inhibition of activation via CD86. Shown are mean±SD on duplicates in 2 independent experiments of the Absorbance measurement corresponding to IL-2 concentration in supernatants.

2C8 was able to restore the secretion of IL-2 by Jurkat T cells in a dose-dependent manner after stimulation via CD80 (FIG. 11) or via CD86 (FIG. 12) and inhibition with CTLA-4.

The assay was repeated several times and consistently showed the ability of 2C8 and derived antibodies to suppress the CTLA-4-mediated inhibition (FIG. 19). In these assays, 2C8 showed an EC50 ranging from 0.6 to 2.0 nM, very similar to Ipilimumab that showed EC50 comprised between 0.5 and 1.4 nM. The LALA mutation did not affect the potency of the antibody as 2C8 with the mutation showed EC50 between 0.7 and 1.2 nM. The germline version of the antibody showed a higher EC50 in one experiment (5.6 nM) and a comparable EC50 otherwise (1.1 nM), this might not be significant.

Example 12: Analysis of In Vivo Activity of
Anti-CTLA-4 Antibody 2C8

The activity of 2C8 was also tested in vivo in a mouse model of tumour growth, using colon carcinoma MC38 cells. Mice were inoculated subcutaneously with $2\times10^6$ MC38 cells at day 0. Starting at day 8, mice were injected intraperitoneally with five doses (200 µg per animal) of 2C8 IgG1 or IgG1 isotype control antibody. Tumour size was measured throughout the experiment.

Figure 13A:
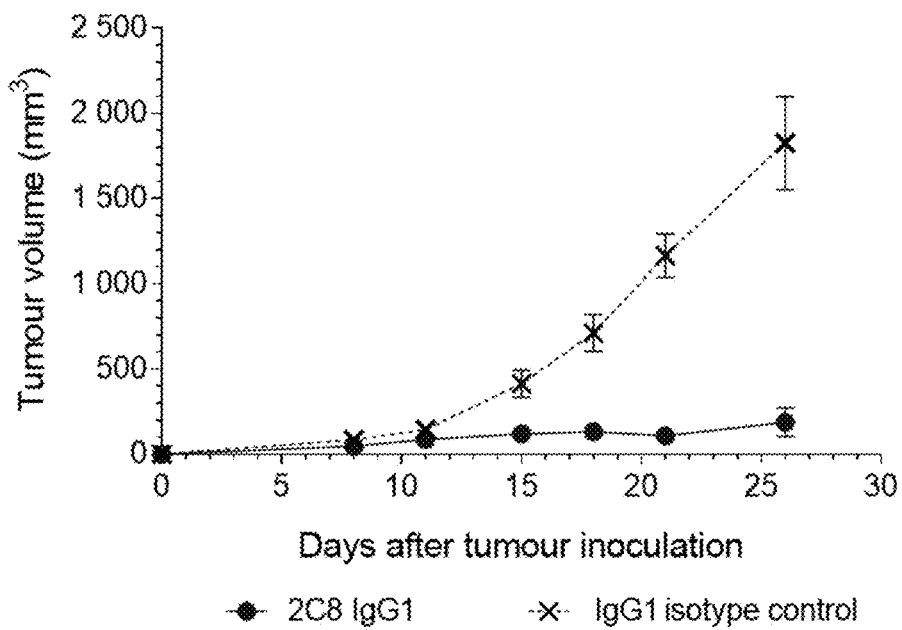
FIG. 13. Graphs showing results of analysis of antitumour activity of 2C8 in vivo in a MC38 tumour growth mouse model of colon carcinoma. (A) and (B) show the results of two independent experiments.
Figure 13B:
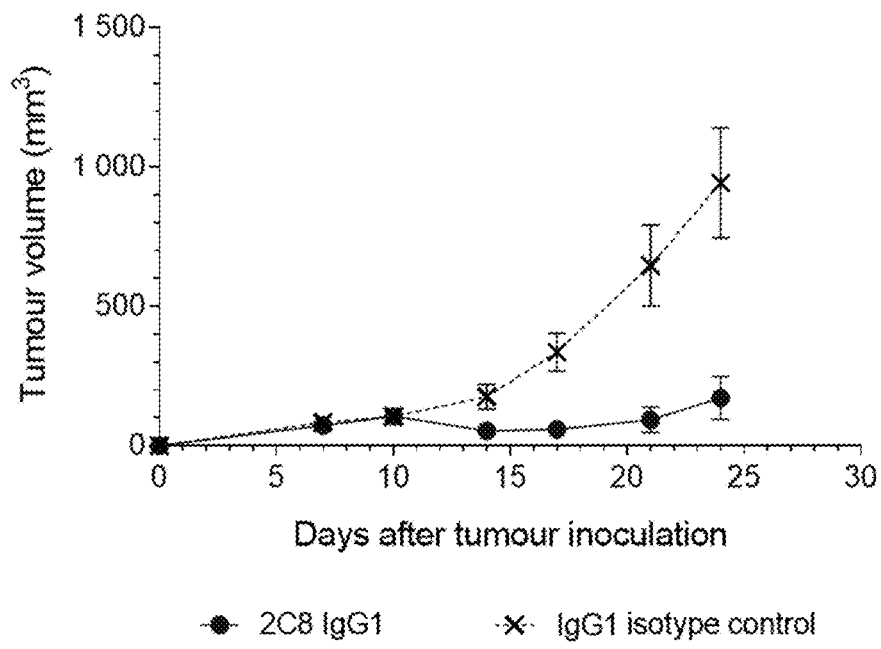

The results of two independent experiments are shown in FIGS. 13A and 13B. 2C8 was shown to be efficient at controlling tumour growth.

The invention claimed is:

1. An antibody, or antigen binding fragment, which is capable of binding to CTLA-4, having at least one light chain variable region incorporating the following CDRs:

```
LC-CDR1:
                         (SEQ ID NO: 5)
RATQGISSWLA

LC-CDR2:
                         (SEQ ID NO: 6)
AASSLQS

LC-CDR3:
                         (SEQ ID NO: 7)
QQANTLPLFT;
``` and having at least one heavy chain variable region incorporating the following CDRs:

```
HC-CDR1:
                         (SEQ ID NO: 8)
SNTAAWN

HC-CDR2:
                         (SEQ ID NO: 9)
RTYYRSKWYSDYGLSVKS

HC-CDR3:
                         (SEQ ID NO: 10)
EGSGGTLIY.
```

2. The antibody or antigen binding fragment of claim 1, comprising a light chain variable region sequence and a heavy chain variable region sequence, wherein:
the light chain variable region sequence has at least 70% sequence identity to the light chain sequence of SEQ ID NO:1 or 2; and
the heavy chain variable region sequence has at least 70% sequence identity to the heavy chain sequence of SEQ ID NO:3 or 4.

3. The antibody, or antigen binding fragment, according to claim 1, wherein the antibody or antigen binding fragment does not bind to CD28.

4. The antibody, or antigen binding fragment, according to claim 1, wherein the antibody or antigen binding fragment inhibits interaction between CTLA-4 and CD80, optionally human CTLA-4 and human CD80.

5. The antibody or antigen binding fragment, according to claim 1, wherein the antibody or antigen binding fragment inhibits interaction between CTLA-4 and CD86, optionally human CTLA-4 and human CD86.

6. The antibody, or antigen binding fragment, of claim 1, wherein the antibody is effective to restore T-cell function in T-cells exhibiting T-cell exhaustion or T-cell anergy.

7. The antibody or antigen binding fragment according to claim 1, wherein the antibody or antigen binding fragment is a bispecific antibody or a bispecific antigen binding fragment comprising (i) an antigen binding fragment according to claim 1, and (ii) an antigen binding fragment which is capable of binding to a target protein other than CTLA-4.

8. The antibody, or antigen binding fragment, of claim 7, wherein the antigen binding fragment which is capable of binding to a target protein other than CTLA-4 is capable of binding to one of PD-1, PD-L1, CD27, CD28, ICOS, CD40, CD122, OX43, 4-1BB, GITR, B7-H3, B7-H4, BTLA, LAG-3, A2AR, VISTA, TIM-3, KIR, HER-2, HER-3, EGFR, EpCAM, CD30, CD33, CD38, CD20, CD24, CD90, CD15, CD52, CA-125, CD34, CA-15-3, CA-19-9, CEA, CD99, CD117, CD31, CD44, CD123, CD133, ABCB5 and CD45.

9. The antibody or antigen binding fragment according to claim 1, wherein the antibody comprises a human constant region selected from IgG1, IgG2, IgG3 and IgG4.

10. The antibody or antigen binding fragment according to claim 1, wherein the antibody fragment is a Fab fragment or an scFv fragment.

11. A method, in vitro or in vivo, of enhancing T-cell function comprising administering an antibody or antigen binding fragment which is capable of binding to CTLA-4, wherein the antibody or antigen binding fragment comprises at least one light chain variable region incorporating the following CDRs:

```
LC-CDR1:
                         (SEQ ID NO: 5)
RATQGISSWLA

LC-CDR2:
                         (SEQ ID NO: 6)
AASSLQS

LC-CDR3:
                         (SEQ ID NO: 7)
QQANTLPLFT;
``` and at least one heavy chain variable region incorporating the following CDRs:

```
HC-CDR1:
                         (SEQ ID NO: 8)
SNTAAWN

HC-CDR2:
                         (SEQ ID NO: 9)
RTYYRSKWYSDYGLSVKS

HC-CDR3:
                         (SEQ ID NO: 10)
EGSGGTLIY.
```

12. The method according to claim 11, wherein the antibody or antigen binding fragment comprises a light chain variable region sequence and a heavy chain variable region sequence, wherein:

the light chain variable region sequence has at least 70% sequence identity to the light chain sequence of SEQ ID NO:1 or 2; and the heavy chain variable region sequence has at least 70% sequence identity to the heavy chain sequence of SEQ ID NO:3 or 4.

13. A method of blocking or reversing T-cell exhaustion in a patient suffering from T-cell exhaustion, comprising administering an antibody or antigen binding fragment which is capable of binding to CTLA-4 to a patient suffering from T-cell exhaustion, wherein the antibody or antigen binding fragment comprises at least one light chain variable region incorporating the following CDRs:

```
LC-CDR1:                        (SEQ ID NO: 5)
RATQGISSWLA

LC-CDR2:                        (SEQ ID NO: 6)
AASSLQS

LC-CDR3:                        (SEQ ID NO: 7)
QQANTLPLFT;
``` and at least one heavy chain variable region incorporating the following CDRs:

```
HC-CDR1:    SNTAAWN              (SEQ ID NO:8)

HC-CDR2:    RTYYRSKWYSDYGLSVKS   (SEQ ID NO:9)

HC-CDR3:    EGSGGTLIY            (SEQ ID NO:10).
```

14. The method according to claim 13, wherein the antibody or antigen binding fragment comprises a light chain variable region sequence and a heavy chain variable region sequence, wherein:

the light chain variable region sequence has at least 70% sequence identity to the light chain sequence of SEQ ID NO:1 or 2; and the heavy chain variable region sequence has at least 70% sequence identity to the heavy chain sequence of SEQ ID NO:3 or 4.

* * * * *

```
SEQUENCE LISTING

<160> NUMBER OF SEQ ID NOS: 14

<210> SEQ ID NO 1
<211> LENGTH: 108
<212> TYPE: PRT
<213> ORGANISM: Artificial Sequence
<220> FEATURE:
<223> OTHER INFORMATION: anti-CTLA-4 antibody 2C8 clone light chain
      variable domain

<400> SEQUENCE: 1

Asp Ile Gln Leu Thr Gln Ser Pro Ser Ser Val Ser Ala Ser Val Gly
1               5                   10                  15

Asp Arg Val Thr Ile Thr Cys Arg Ala Thr Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Thr Leu Pro Leu
                85                  90                  95

Phe Thr Phe Gly Pro Gly Thr Lys Val Asp Ile Lys
                100                 105

<210> SEQ ID NO 2
<211> LENGTH: 108
<212> TYPE: PRT
<213> ORGANISM: Artificial Sequence
<220> FEATURE:
<223> OTHER INFORMATION: anti-CTLA-4 antibody 2C8 gl clone light chain
      variable domain

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Thr Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Leu Pro Leu
                85                  90                  95

Phe Thr Phe Gly Pro Gly Thr Lys Val Asp Ile Lys
                100                 105

<210> SEQ ID NO 3
<211> LENGTH: 121
<212> TYPE: PRT
```

<213> ORGANISM: Artificial Sequence
<220> FEATURE:
<223> OTHER INFORMATION: anti-CTLA-4 antibody 2C8 clone heavy chain
     variable domain

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Thr Val Ser Ser Asn
            20                  25                  30

Thr Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Asp Tyr Gly
    50                  55                  60

Leu Ser Val Lys Ser Arg Met Thr Ile Asn Ala Asp Thr Ser Lys Asn
65                  70                  75                  80

Gln Val Ser Leu His Leu Asn Ser Val Thr Pro Glu Asp Thr Ala Val
                85                  90                  95

Tyr Tyr Cys Ala Arg Glu Gly Ser Gly Gly Thr Leu Ile Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: anti-CTLA-4 antibody 2C8 g1 clone heavy chain
     variable domain

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Thr Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Asp Tyr Gly
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Ser Gly Gly Thr Leu Ile Tyr Trp Gly
            100                 105                 110

Gln Gly Thr Leu Val Thr Val Ser Ser
        115                 120

<210> SEQ ID NO 5
<211> LENGTH: 11
<212> TYPE: PRT
<213> ORGANISM: Artificial Sequence
<220> FEATURE:
<223> OTHER INFORMATION: anti-CTLA-4 antibody 2C8 clone light chain
     variable domain LC-CDR1

<400> SEQUENCE: 5

Arg Ala Thr Gln Gly Ile Ser Ser Trp Leu Ala
1               5                   10

```
<210> SEQ ID NO 6
<211> LENGTH: 7
<212> TYPE: PRT
<213> ORGANISM: Artificial Sequence
<220> FEATURE:
<223> OTHER INFORMATION: anti-CTLA-4 antibody 2C8 clone light chain
      variable domain LC-CDR2

<400> SEQUENCE: 6

Ala Ala Ser Ser Leu Gln Ser
1               5

<210> SEQ ID NO 7
<211> LENGTH: 10
<212> TYPE: PRT
<213> ORGANISM: Artificial Sequence
<220> FEATURE:
<223> OTHER INFORMATION: anti-CTLA-4 antibody 2C8 clone light chain
      variable domain LC-CDR3

<400> SEQUENCE: 7

Gln Gln Ala Asn Thr Leu Pro Leu Phe Thr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: anti-CTLA-4 antibody 2C8 clone heavy chain
      variable domain LC-CDR1

<400> SEQUENCE: 8

Ser Asn Thr Ala Ala Trp Asn
1               5

<210> SEQ ID NO 9
<211> LENGTH: 18
<212> TYPE: PRT
<213> ORGANISM: Artificial Sequence
<220> FEATURE:
<223> OTHER INFORMATION: anti-CTLA-4 antibody 2C8 clone heavy chain
      variable domain LC-CDR2

<400> SEQUENCE: 9

Arg Thr Tyr Tyr Arg Ser Lys Trp Tyr Ser Asp Tyr Gly Leu Ser Val
1               5                   10                  15

Lys Ser

<210> SEQ ID NO 10
<211> LENGTH: 9
<212> TYPE: PRT
<213> ORGANISM: Artificial Sequence
<220> FEATURE:
<223> OTHER INFORMATION: anti-CTLA-4 antibody 2C8 clone heavy chain
      variable domain LC-CDR3

<400> SEQUENCE: 10

Glu Gly Ser Gly Gly Thr Leu Ile Tyr
1               5

<210> SEQ ID NO 11
<211> LENGTH: 324
<212> TYPE: DNA
<213> ORGANISM: Artificial Sequence
<220> FEATURE:
```

<223> OTHER INFORMATION: anti-CTLA-4 antibody 2C8 clone light chain
       variable domain

<400> SEQUENCE: 11
gacatccagt tgacccagtc tccatcttct gtgtctgcat ctgtgggaga cagagtcacc        60
atcacttgtc gggcgactca gggtataagc agctggttag cctggtatca gcagaaacca       120
gggaaagccc ctaagctcct gatctatgct gcatccagtt tgcaaagtgg ggtcccatcc       180
aggttcagcg gcagtggctc tgggacagag ttcactctca ctatcagcag cctgcagcct       240
gaagattttg caacttacta ttgtcaacag gctaatactc tccccttatt cactttcggc       300
cctgggacca aagtggatat caaa                                              324

<210> SEQ ID NO 12
<211> LENGTH: 324
<212> TYPE: DNA
<213> ORGANISM: Artificial Sequence
<220> FEATURE:
<223> OTHER INFORMATION: anti-CTLA-4 antibody 2C8 gl clone light chain
       variable domain

<400> SEQUENCE: 12
gacatccaga tgacccagtc tccatcttct gtgtctgcat ctgtgggaga cagagtcacc        60
atcacttgtc gggcgactca gggtataagc agctggttag cctggtatca gcagaaacca       120
gggaaagccc ctaagctcct gatctatgct gcatccagtt tgcaaagtgg ggtcccatcc       180
aggttcagcg gcagtggctc tgggacagat ttcactctca ctatcagcag cctgcagcct       240
gaagattttg caacttacta ttgtcaacag gctaatactc tccccttatt cactttcggc       300
cctgggacca aagtggatat caaa                                              324

<210> SEQ ID NO 13
<211> LENGTH: 363
<212> TYPE: DNA
<213> ORGANISM: Artificial Sequence
<220> FEATURE:
<223> OTHER INFORMATION: anti-CTLA-4 antibody 2C8 clone heavy chain
       variable domain

<400> SEQUENCE: 13
caggtacagc tgcagcagtc aggtccagga ctggtgaagc cctcgcagac cctctcactc        60
acctgcgcca tctccgggga cactgtctct agcaacactg ctgcttggaa ttggatcagg       120
cagtccccct cgagaggcct tgagtggctg ggaaggacat actacaggtc aagtggtat        180 agtgactatg gactatctgt gaaaagtcgg atgaccatca tgcagacac atccaagaac        240 caggtctccc tacacctgaa ctctgtaact cccgaagaca cggctgtata ttactgtgca       300
agagagggca gtggcggaac tttgatctac tggggccagg gaaccctggt caccgtctca       360
agc                                                                     363

<210> SEQ ID NO 14
<211> LENGTH: 363
<212> TYPE: DNA
<213> ORGANISM: Artificial Sequence
<220> FEATURE:
<223> OTHER INFORMATION: anti-CTLA-4 antibody 2C8 gl clone heavy chain
       variable domain

<400> SEQUENCE: 14
caggtacagc tgcagcagtc aggtccagga ctggtgaagc cctcgcagac cctctcactc        60
acctgcgcca tctccgggga cagtgtctct agcaacactg ctgcttggaa ttggatcagg       120

```
cagtccccct cgagaggcct tgagtggctg ggaaggacat actacaggtc caagtggtat        180
agtgactatg gactatctgt gaaaagtcgg ataaccatca atccagacac atccaagaac        240
cagttctccc tacagctgaa ctctgtaact cccgaagaca cggctgtata ttactgtgca        300
agagagggca gtggcggaac tttgatctac tggggccagg gaaccctggt caccgtctca        360
agc                                                                     363
```